(12) United States Patent
Park et al.

(10) Patent No.: US 9,758,771 B2
(45) Date of Patent: Sep. 12, 2017

(54) MICROORGANISM WITH ENHANCED L-LYSINE PRODUCTIVITY AND METHOD FOR PRODUCING L-LYSINE BY USING SAME

(71) Applicant: CJ CHEILJEDANG CORPORATION, Seoul (KR)

(72) Inventors: Sang Hee Park, Seoul (KR); Jun Ok Moon, Seoul (KR); Kwang Ho Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/392,186

(22) PCT Filed: Jun. 24, 2014

(86) PCT No.: PCT/KR2014/005576
§ 371 (c)(1),
(2) Date: Dec. 23, 2015

(87) PCT Pub. No.: WO2014/208981
PCT Pub. Date: Dec. 31, 2014

(65) Prior Publication Data
US 2016/0230151 A1    Aug. 11, 2016

(30) Foreign Application Priority Data

Jun. 25, 2013 (KR) .................. 10-2013-0073309

(51) Int. Cl.
*C12N 9/12* (2006.01)
*C12P 13/08* (2006.01)
*C12N 15/77* (2006.01)

(52) U.S. Cl.
CPC .......... *C12N 9/1247* (2013.01); *C12N 15/77* (2013.01); *C12P 13/08* (2013.01); *C12Y 207/07006* (2013.01)

(58) Field of Classification Search
None
See application file for complete search history.

(56) References Cited

U.S. PATENT DOCUMENTS

2012/0220000 A1    8/2012    Gong et al.

FOREIGN PATENT DOCUMENTS

| KR | 1020100000665 | 1/2010 |
|---|---|---|
| KR | 1020120099258 | 9/2012 |
| WO | 0149854 | 7/2001 |
| WO | 03055996 A1 | 7/2003 |
| WO | 2011063055 A2 | 5/2011 |

OTHER PUBLICATIONS

Stephan Binder et al., A high-throughput approach to identify genomic variants of bacterial metabolite producers at the single-cell level, Article, 2012, 13, pp. 1-12, Genome Biology.
Extended European Search Report for Application No. 14817261.2 dated Dec. 1, 2016.
Chhabra, Swapnil R., "Metabolic Design and Control for Production in Prokaryotes", Lawrence Berkeley National Laboratory, Jun. 16, 2011, pp. 1-52.
DNA-directed RNA polymerase beta'subunit [Corynebacterium glutamicum], Posted May 19, 2013, pp. 1-3, Retrieved from the Internet Sep. 29, 2014, <URL:http://www.ncbi.nlm.nih.gov/protein/505252318?report=genbank&log$=protalign&b . . . >.
International Search Report—PCT/KR2014/005576 dated Sep. 29, 2014.
Korean Office Action—KR Application No. 10-2013-0073309 dated Feb. 24, 2015, citing 10-2012-0099258.
Written Opinion—PCT/KR2014/005576 dated Sep. 29, 2014.

*Primary Examiner* — Richard Hutson
(74) *Attorney, Agent, or Firm* — Cantor Colburn LLP

(57) ABSTRACT

Provided are a beta prime subunit mutant of RNA polymerase, a microorganism of the *Corynebacterium* genus including a polynucleotide coding the same, and a method for producing L-lysine by culturing the same.

6 Claims, 4 Drawing Sheets

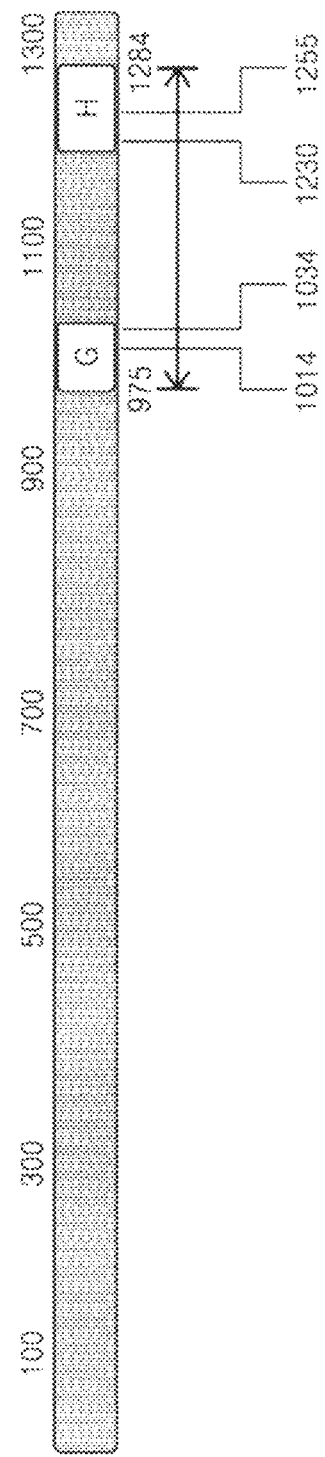

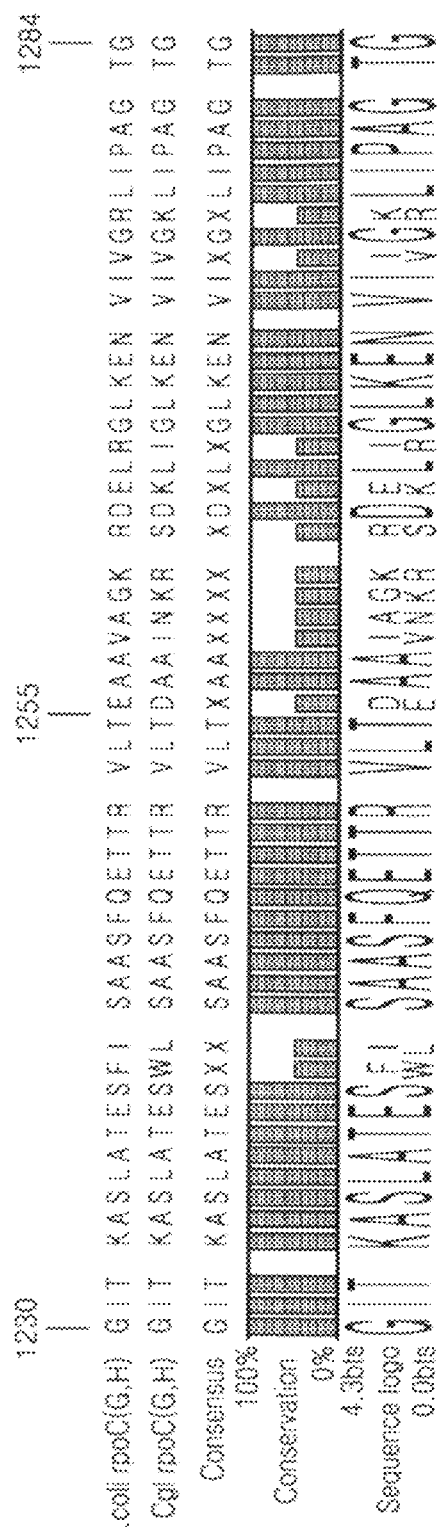

MICROORGANISM WITH ENHANCED L-LYSINE PRODUCTIVITY AND METHOD FOR PRODUCING L-LYSINE BY USING SAME

TECHNICAL FIELD

The present application relates to a microorganism with enhanced L-lysine productivity and a method for producing L-lysine by using the same.

BACKGROUND ART

World widely, a variety of fermentation methods using microorganisms have been used for mass-production of useful products such as amino acids, etc. In particular, many technologies including the development of bacterial strains and establishment of fermentation conditions have been developed for successful fermentation using microorganisms. To develop bacterial strains for mass-production of useful products, genetic factors directly or indirectly involved in the upstream of glycolytic pathway are properly used to develop a strain with a higher efficiency. A representative technique is global Transcription Machinery Engineering (gTME) which induces random mutations in recruiting proteins of RNA polymerase to regulate all genetic expressions in cells.

RNA polymerase used in a transcription step of a microorganism is a macromolecule consisting of 5 subunits; two alpha, beta, beta prime, and sigma subunits. Its holoenzyme is expressed as $\alpha 2\beta\beta'\sigma$. Of them, a core enzyme ($\alpha 2\beta\beta'$) is used in all transcription steps, excluding the step of transcription initiation. In microorganisms, transcription begins with the specific binding of RNA polymerase to a promoter, and the holoenzyme binds with DNA in the region about 45 base pairs upstream and about 10 base pairs downstream from the initiation point of RNA polymerization.

Beta prime subunit of RNA polymerase of *E. coli* has an evolutionarily highly conserved region of A~H. Many studies have reported that induction of mutations in this region causes different changes such as weakening of binding of RNA polymerase with other factors, increase in growth temperature sensitivity of the strain, etc. However, there have been no studies about the application of gTME to a bacterial strain belonging to the genus *Corynebacterium* and changes in characteristics by mutations.

Genes encoding beta and beta prime subunits of the subunits constituting RNA polymerase of a bacterial strain belonging to the genus *Corynebacterium*, namely, rpoB and rpoC, form an operon, and they consist of nucleotides of 3.5 kb and 4.0 kb, respectively.

The present inventors introduced random mutations into rpoC, which is derived from the bacterial strain belonging to the genus *Corynebacterium*, and screened a mutant that contributes to the improvement of L-lysine productivity. They found that the introduction of mutations into the regions corresponding to G and H of *E. coli*-derived rpoC greatly improves lysine productivity, thereby completing the present application.

DETAILED DESCRIPTION OF THE INVENTION

Technical Problem

An aspect provides a beta prime subunit mutant of RNA polymerase, which is able to increase L-lysine production.

Another aspect provides a polynucleotide having a nucleotide sequence encoding the beta prime subunit mutant of RNA polymerase, which is able to increase L-lysine production.

Still another aspect provides a vector including the polynucleotide having the nucleotide sequence encoding the beta prime subunit mutant of RNA polymerase, which is able to increase L-lysine production.

Still another aspect provides a microorganism including the beta prime subunit mutant.

Still another aspect provides a method of producing L-lysine by culturing the microorganism.

Technical Solution

An aspect provides a beta prime subunit ($\beta'$-subunit) of RNA polymerase, in which 1 to 5 amino acids at positions 975 to 1284 in an amino acid sequence represented by SEQ ID NO: 1 are substituted with other amino acids.

The beta prime subunit may be RpoC protein. The RpoC protein may include a conserved region. The conserved region may be an evolutionarily highly conserved region. The RpoC protein may include a plurality of domains. The plurality of domains may be A to H domains. The beta prime subunit may be derived from a microorganism belonging to the genus *Corynebacterium*. An amino acid sequence of the beta prime subunit derived from the microorganism belonging to the genus *Corynebacterium* may be represented by SEQ ID NO: 1 or may have about 70% or higher, about 75% or higher, about 80% or higher, about 85% or higher, about 90% or higher, about 92% or higher, about 95% or higher, about 97% or higher, about 98% or higher, or about 99% or higher sequence homology with SEQ ID NO: 1. A sequence having a homology with amino acids at positions 975 to 1284 in the amino acid sequence of the beta prime subunit derived from the microorganism belonging to the genus *Corynebacterium*, that is, the RpoC amino acid sequence, may be an *E. coli*-derived RpoC amino acid sequence. The RpoC amino acid sequence of *E. coli* including G and H domains may be represented by SEQ ID NO: 4.

1 to 5 amino acids in the amino acid sequences of G domain and H domain of beta prime subunit represented by SEQ ID NO: 1 may be substituted with other amino acids. Specifically, 1 to 5 amino acids at positions 975 to 1284 in the amino acid sequence represented by SEQ ID NO. 1 may be substituted with other amino acids. More specifically, 1 to 5 amino acids at positions 1014 to 1034 or at positions 1230 to 1255 in the amino acid sequence represented by SEQ ID NO. 1 may be substituted with other amino acids. SEQ ID NO: 8, 9, 11, 14, 15, 20, 23, 24, or 25 may be an amino acid sequence resulting from the substitution of 1 to 5 amino acids at positions 1014 to 1034 in the amino acid sequence represented by SEQ ID NO. 1 with other amino acids. SEQ ID NO: 10, 12, 13, 16, 17, 18, 19, 21, 22, or 27 may be an amino acid sequence resulting from the substitution of 1 to 5 amino acids at positions 1230 to 1255 in the amino acid sequence represented by SEQ ID NO. 1 with other amino acids. SEQ ID NO: 26 may be an amino acid sequence resulting from the substitution of 1 to 5 amino acids at positions 1014 to 1034 and at positions 1230 to 1255 in the amino acid sequence represented by SEQ ID NO. 1 with other amino acids.

A specific embodiment provides a polynucleotide including a nucleotide sequence encoding the beta prime subunit mutant of RNA polymerase, in which 1 to 5 amino acids at positions 975 to 1284 in the amino acid sequence of SEQ ID NO. 1 may be substituted with other amino acids.

Still another aspect provides a vector including the polynucleotide. The polynucleotide may be operably linked to a regulatory sequence. The regulatory sequence may include a promoter, a terminator, or an enhancer. Further, the promoter may be operably linked to a sequence encoding a gene. As used herein, the term "operably linked" may refer to a functional linkage between a nucleic acid expression control sequence and another nucleotide sequence, whereby the control sequence directs transcription and/or translation of the nucleotide sequence encoding the gene.

Still another aspect provides a microorganism expressing the beta prime subunit mutant of RNA polymerase, in which 1 to 5 amino acids at positions 975 to 1284 in the amino acid sequence represented by SEQ ID NO. 1 is/are substituted with other amino acids.

Provided is a microorganism including a polynucleotide having a nucleotide sequence encoding the beta prime subunit mutant of RNA polymerase, in which 1 to 5 amino acids at positions 975 to 1284 in the amino acid sequence represented by SEQ ID NO. 1 is/are substituted with other amino acids. Provided is also a microorganism which is introduced with the vector including the polynucleotide having the nucleotide sequence encoding the beta prime subunit mutant of RNA polymerase, in which 1 to 5 amino acids at positions 975 to 1284 in the amino acid sequence represented by SEQ ID NO. 1 is/are substituted with other amino acids. The introduced microorganism may be a transformed microorganism.

Introduction of the gene may be introduction of any form, for example, introduction of an expression cassette, introduction of a gene in itself, or introduction of a polynucleotide construct. The expression cassette may include all elements required for self-expression of the gene. The expression cassette may be a polynucleotide construct. The expression cassette may include a promoter, a transcription termination signal, a ribosome binding site, and a translation termination signal, which are operably linked to the gene. The expression cassette may be in the form of a self-replicable expression vector. The gene itself or the polynucleotide structure may be introduced into a host cell to be operably linked to a sequence required for expression in the host cell.

As used herein, the term "transformation" means introducing a gene into a host cell so that the gene is expressed therein. The transformed gene may be integrated into the host chromosome or/and exit as an extrachromosomal element. The gene may be a polynucleotide encoding a polypeptide. The gene includes DNA or RNA.

The microorganism may be a microorganism belonging to the genus *Corynebacterium*. The microorganism belonging to the genus *Corynebacterium* may include *Corynebacterium glutamicum, Corynebacterium efficiens, Corynebacterium diphtheriae*, or *Corynebacterium ammoniagenes*, and it may be specifically *Corynebacterium glutamicum*. Specifically, the microorganism belonging to the genus *Corynebacterium* may be a *Corynebacterium glutamicum* with Accession No. KCCM11016P, KCCM11347P (International deposit of KFCC10750), KCCM10770, or CJ3P.

Still another aspect provides a method for producing L-lysine, the method including the steps of culturing a microorganism expressing the beta prime subunit mutant of RNA polymerase, in which 1 to 5 amino acids at positions 975 to 1284 in the amino acid sequence represented by SEQ ID NO. 1 is/are substituted with other amino acids, so as to produce L-lysine in culture medium; and recovering L-lysine from the culture medium. The microorganism is the same as described above. Culturing the microorganism may be performed in a proper medium under culture conditions that are well known in the art. Such culturing process may be easily adjusted depending on a microorganism to be selected. The culturing method may include one or more selected from the group consisting of batch culture, continuous culture, and fed-batch culture.

The medium used in culturing may meet the requirements of a particular microorganism. The medium may be selected from the group consisting of carbon sources, nitrogen sources, trace elements, and combinations thereof.

The carbon source may be selected from the group consisting of carbohydrates, lipids, fatty acids, alcohols, organic acids, and combinations thereof. The carbohydrate may be glucose, sucrose, lactose, fructose, maltose, starch, cellulose, or a combination thereof. The lipid may be soybean oil, sunflower oil, castor oil, coconut oil, or a combination thereof. The fatty acid may be palmitic acid, stearic acid, linoleic acid, or a combination thereof. The alcohol may be glycerol or ethanol. The organic acid may be acetic acid.

The nitrogen source may include an organic nitrogen source, an inorganic nitrogen source, or a combination thereof. The organic nitrogen source may be selected from the group consisting of peptone, yeast extract, meat extract, malt extract, corn steep liquid (CSL), soybean meal, and combinations thereof. The inorganic nitrogen source may be selected from the group consisting of urea, ammonium sulfate, ammonium chloride, ammonium phosphate, ammonium carbonate, ammonium nitrate, and combinations thereof.

The medium may include one selected from the group consisting of phosphorous, metal salts, amino acids, vitamins, precursors, and combinations thereof. The phosphorous source may include potassium dihydrogen phosphate, dipotassium phosphate, a sodium-containing salt corresponding thereto. The metal salt may be magnesium sulfate and iron sulfate.

The medium or individual components may be added to the culture medium in a batch mode, a continuous mode, or a fed-batch mode.

In the culturing method, the pH of the culture may be adjusted. The pH adjustment may be performed by adding ammonium hydroxide, potassium hydroxide, ammonia, phosphoric acid, or sulfuric acid to the culture. Further, the culturing method may include prevention of air bubbles generation. The prevention of air bubbles generation may be performed by using an antifoaming agent. The antifoaming agent may include fatty acid polyglycol ester. Further, the culturing method may include injection of gas into the culture. The gas may include any gas to maintain the aerobic condition of the culture. The gas may be oxygen or oxygen-containing gas. The oxygen-containing gas may include air. In the culturing, the temperature of the culture may be 20 to 45° C., for example, 22 to 42° C., or 25 to 40° C. The culturing may be continued until the production of L-lysine reaches a desired level.

In the method of producing L-lysine, the L-lysine may include salts of L-lysine.

Advantageous Effects of the Application

Production of L-lysine may be increased by using a beta prime subunit of RNA polymerase according to an aspect, a polynucleotide encoding the same, a vector including the polynucleotide, and a microorganism.

Production of L-lysine may be increased by a method of producing L-lysine according to an aspect.

MODE OF THE INVENTION

Figure 1A:
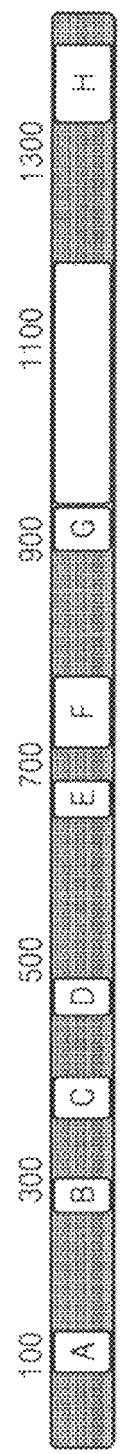
FIG. 1 shows a conserved sequence structure of RpoC protein of *E. coli*, and a predicted conserved sequence structure of RpoC protein of *Corynebacterium*.

Hereinafter, the present application will be described in more detail with reference to Examples. However, these Examples are for illustrative purposes only, and the scope of the present application is not intended to be limited by these Examples.

Example 1: Construction of rpoC Mutant Library by Artificial Mutagenesis

To obtain an rpoC gene mutant, a vector library was constructed by the following method. A base sequence (4302 bp) including an upstream base sequence (300 bp) of *Corynebacterium*-derived rpoC gene (SEQ ID NO: 5) and rpoC (4002 bp) gene was amplified by error-prone PCR using the chromosome of KCCM11016P (International deposit of KFCC10881 of Korean Patent Publication No. KR2007-0057093) as a template and primers of SEQ ID NOS: 6 and 7. For the purpose of introducing 0-4.5 mutations per kb into the amplified gene, a GenemorphII Random Mutagenesis Kit (Stratagene) was used. 50 uL of a reaction solution containing 500 ng of the chromosome of KCCM11016P strain, each 125 ng of primers 1 and 2, 1× Mutazyme II reaction buffer, 40 mM dNTPs (deoxyNucleotide-Triphosphates) mix, 2.5 U of Mutazyme II DNA polymerase was subjected to denaturation at 94° C. for 2 minutes, 25 cycles of denaturation at 94° C. for 1 minute, annealing at 56° C. for 1 minute, and polymerization at 72° C. for 4 minutes, and then polymerization at 72° C. for 10 minutes.

The amplified gene fragment was ligated to a pTOPO vector using a pTOPO TA Cloning Kit (Invitrogen). Thereafter, the vector was transformed into *E. coli* DH5α and spread on an LB solid medium containing 25 mg/l kanamycin. 20 kinds of transformed colonies were selected, and plasmids were obtained therefrom, followed by sequencing analysis. As a result, mutations were found to be introduced into the different sites at a frequency of 0.5 mutation/kb. About 10,000 of transformed *E. coli* colonies were taken and plasmids were extracted therefrom, which were designated as pTOPO-rpoC(M) library. A pTOPO-rpoC(W) plasmid having a wild-type rpoC gene was also prepared as a control group. An rpoC gene fragment was amplified by PCR using the chromosome of KCCM11016P as a template and primers of SEQ ID NOS: 6 and 7, and then a pTOPO-rpoC(W) plasmid was prepared in the same manner.

Example 2: Screening of rpoC Mutant Based on Lysine Productivity

KCCM11016P strain as a parent strain was transformed with pTOPO-rpoC(M) library and spread on a complex medium plate containing kanamycin (25 mg/l) to obtain about 21,500 colonies.

<Complex Medium Plate (pH 7.0)>
10 g of glucose, 10 g of peptone, 5 g of beef extract, 5 g of yeast extract, 18.5 g of Brain Heart Infusion, 2.5 g of NaCl, 2 g of urea, 91 g of sorbitol, 20 g of agar (based on 1 L of distilled water)

<Seed Medium (pH 7.0)>
20 g of glucose, 10 g of peptone, 5 g of yeast extract, 1.5 g of urea, 4 g of $KH_2PO_4$, 8 g of $K_2HPO_4$, 0.5 g of $MgSO_4.7H_2O$, 100 μg of biotin, 1000 μg of thiamine HCl, 2000 μg of calcium pantothenate, 2000 μg of nicotinamide (based on 1 L of distilled water)

About 21,500 colonies thus obtained were inoculated in 300 uL of a selection medium, respectively and cultured in a 96-well plate at 32° C., 1000 rpm for about 24 hours. To analyze a production amount of L-lysine in the culture, a ninhydrin method was used. After completing the culture, 10 ul of a culture supernatant and 190 ul of a ninhydrin reaction solution were reacted at 65° C. for 30 minutes, and then absorbance was measured at a wavelength of 570 nm using a spectrophotometer to select about 2,000 mutant colonies showing higher absorbance than a control group, KCCM11016P-rpoC(W) having a wild-type rpoC. Other colonies showed similar absorbance to KCCM11016P or KCCM11016P-rpoC(W) used as a control group. From the selected 2000 colonies, the top 183 strains showing enhanced L-lysine productivity, compared to the KCCM11016P-rpoC(W) strain, were selected by the ninhydrin reaction in the same manner.

<Selection Medium (pH 8.0)>
10 g of glucose, 5.5 g of ammonium sulfate, 1.2 g of $MgSO_4.7H_2O$, 0.8 g of $KH_2PO_4$, 16.4 g of $K_2HPO_4$, 100 μg of biotin, 1000 mg of thiamine HCl, 2000 μg of calcium pantothenate, 2000 μg of nicotinamide (based on 1 L of distilled water)

Example 3: Identification of Gene Mutations in Selected Strains from rpoC Artificial Mutant Library To figure out characters of the strains selected in Example 2, sequencing analysis was performed. To find out mutations, a base sequence of the rpoC chromosomal region of KCCM11016P-rpoC(M) was determined, and identified based on the NIH GenBank (US).

FIG. 1b shows a conserved sequence structure of RpoC protein of *E. coli*, and a predicted conserved sequence structure of RpoC protein of *Corynebacterium*. According to FIG. 1b, the results of homology analysis of the base sequence of the selected mutant rpoC showed that mutations are concentrated at positions 975 to 1284 of the amino acid sequence of SEQ ID NO: 1 encoded by rpoC in 166 strains corresponding to 91% of 183 strains. It was also found that mutations are concentrated in a small region at positions 1014 to 1034 and at positions of 1230 to 1255 of the amino acid sequence in 116 strains corresponding to about 70% of 166 strains.

Figure 2A:
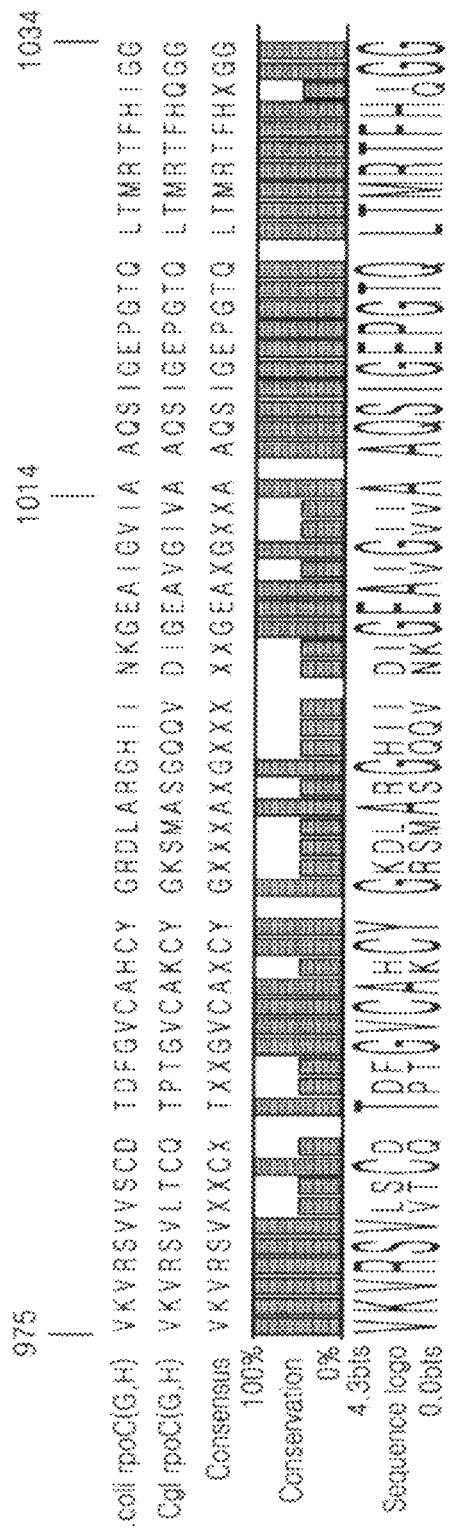
FIG. 2 is a comparison between predicted amino acid sequences of G and H conserved regions of *Corynebacterium* RpoC and *E. coli* RpoC.

To figure out characters of the region in which mutations are concentrated, amino acid sequences were compared between *Corynebacterium* RpoC and RNA polymerase beta prime subunit of *E. coli* actively studied. FIG. 2 is a comparison between predicted amino acid sequences of G and H conserved regions of *E. coli* RpoC and *Corynebacterium* RpoC. According to FIG. 2, it showed 68.4% and 77.8% homology to G and H domains among 8 domains which are known as evolutionarily highly conserved sequence of the RNA polymerase beta prime subunit of *E. coli*. FIG. 1 shows a conserved sequence structure of RpoC protein of *E. coli*, and a predicted conserved sequence structure of RpoC protein of *Corynebacterium*. According to FIG. 1b, mutations were found to be concentrated at positions 975 to 1284 of *Corynebacterium* RpoC protein, this region showing high homology to G and H domains of rpoC, which is an RNA polymerase beta prime subunit of *E. coli*. Among 116 strains, the top 20 strains showing high absorbance in the ninhydrin reaction were designated as KCCM11016P-rpoC(M1)~KCCM11016P-rpoC(M20).

Example 4: Lysine Productivity and Analysis of KCCM11016P-rpoC(M)

To figure out characters of 20 strains of KCCM11016P-rpoC(M1) KCCM11016P-rpoC(M20) selected in Example 3, they were cultured by the following method, their lysine productivities were compared and components in culture broths were analyzed.

The individual strains were inoculated in a 250 ml corner-baffled flask containing 25 ml of a seed medium and cultured with shaking at 200 rpm and 30° C. for 20 hours. 1 ml of the seed medium was inoculated to a 250 ml corner-baffled flask containing 24 ml of a production medium and cultured while shaking at 200 rpm and 30° C. for 72 hours. The seed medium and production medium have the following compositions.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4.7H_2O$, 100 μg of biotin, 1000 μg of thiamine HCl, 2000 μg of calcium pantothenate, 2000 μg of nicotinamide (based on 1 L of distilled water)

<Production Medium (pH 7.0)>

100 g of glucose, 40 g of $(NH_4)_2SO_4$, 2.5 g of soy bean protein, 5 g of corn steep solid, 3 g of urea, 1 g of $KH_2PO_4$, 0.5 g of $MgSO_4.H_2O$, 100 μg of biotin, 1000 μg of thiamine HCl, 2000 μg of calcium pantothenate, 3000 μs of nicotinamide, 30 g of $CaCO_3$ (based on 1 L of distilled water)

L-lysine concentrations analyzed by HPLC are given in Table 1.

TABLE 1

Concentrations of L-lysine produced by KCCM11016P-rpoC(M)

| | strain | L-lysine (g/l) | | | |
|---|---|---|---|---|---|
| | | Batch 1 | Batch 2 | Batch 3 | Average |
| Control group | KCCM11016P-rpoC(W) | 43.2 | 44.1 | 43.2 | 42.8 |
| 1 | KCCM11016P-rpoC(M1) | 46.1 | 46.5 | 47.1 | 43.6 |
| 2 | KCCM11016P-rpoC(M2) | 47.7 | 46.3 | 46.8 | 46.9 |
| 3 | KCCM11016P-rpoC(M3) | 48.2 | 48.6 | 48.4 | 48.4 |
| 4 | KCCM11016P-rpoC(M4) | 49 | 48.9 | 48.9 | 48.9 |
| 5 | KCCM11016P-rpoC(M5) | 48.3 | 49.8 | 49.5 | 49.2 |
| 6 | KCCM11016P-rpoC(M6) | 46.2 | 46.9 | 46.7 | 46.6 |
| 7 | KCCM11016P-rpoC(M7) | 45.3 | 45.8 | 45.9 | 45.7 |
| 8 | KCCM11016P-rpoC(M8) | 46.1 | 46.5 | 45.1 | 45.9 |
| 9 | KCCM11016P-rpoC(M9) | 47.3 | 47.9 | 47.9 | 47.7 |
| 10 | KCCM11016P-rpoC(M10) | 48.3 | 48.5 | 47.9 | 48.2 |
| 11 | KCCM11016P-rpoC(M11) | 45.3 | 45.8 | 45.9 | 45.7 |
| 12 | KCCM11016P-rpoC(M12) | 48.6 | 48.3 | 48.3 | 48.4 |
| 13 | KCCM11016P-rpoC(M13) | 46.6 | 47 | 47.1 | 46.9 |
| 14 | KCCM11016P-rpoC(M14) | 47.3 | 48.6 | 48 | 48.0 |
| 15 | KCCM11016P-rpoC(M15) | 49.2 | 49.2 | 49.4 | 49.3 |
| 16 | KCCM11016P-rpoC(M16) | 46.2 | 46.5 | 46 | 46.2 |
| 17 | KCCM11016P-rpoC(M17) | 46.3 | 45.2 | 45.8 | 45.8 |

TABLE 1-continued

Concentrations of L-lysine produced by KCCM11016P-rpoC(M)

| | strain | L-lysine (g/l) | | | |
|---|---|---|---|---|---|
| | | Batch 1 | Batch 2 | Batch 3 | Average |
| 18 | KCCM11016P-rpoC(M18) | 48.3 | 48.2 | 48.3 | 48.3 |
| 19 | KCCM11016P-rpoC(M19) | 47.3 | 47.8 | 47.5 | 47.5 |
| 20 | KCCM11016P-rpoC(M20) | 48.3 | 48.7 | 48.5 | 48.5 |

As shown in Table 1, the average concentration of L-lysine in KCCM11016P-rpoC(M) was increased by 13%, compared to that of an L-lysine-producing strain, KCCM11016P-rpoC(W). Alterations in amino acid sequences of 20 kinds of rpoC mutants are represented by SEQ ID NOS: 8 to 27. The result of analyzing the amino acid sequences of 20 kinds of the mutants showed that lysine productivity is greatly enhanced by introducing mutations into the region at positions 975 to 1284, this region showing high homology to G and H domains of rpoC, which is an RNA polymerase beta prime subunit of *E. coli*.

TABLE 2 rpoC amino acid mutations in KCCM11016P-rpoC(M1)~(M20)

| Strain | rpoC amino acid mutation |
|---|---|
| KCCM11016P-rpoC(M1) | Q1016G |
| KCCM11016P-rpoC(M2) | T1029H |
| KCCM11016P-rpoC(M3) | F1247K |
| KCCM11016P-rpoC(M4) | W24G, G995E, I1018C |
| KCCM11016P-rpoC(M5) | G995H, I1231C |
| KCCM11016P-rpoC(M6) | R1252T |
| KCCM11016P-rpoC(M7) | G1022R |
| KCCM11016P-rpoC(M8) | A1015D |
| KCCM11016P-rpoC(M9) | A1237P |
| KCCM11016P-rpoC(M10) | W1241N |
| KCCM11016P-rpoC(M11) | Y36F, T1255C |
| KCCM11016P-rpoC(M12) | E1249Y, G1282F |
| KCCM11016P-rpoC(M13) | G1022S |
| KCCM11016P-rpoC(M14) | S1243G |
| KCCM11016P-rpoC(M15) | E1239T |
| KCCM11016P-rpoC(M16) | G1034K, D1038H |
| KCCM11016P-rpoC(M17) | L340E, A1014D |
| KCCM11016P-rpoC(M18) | A1015H |
| KCCM11016P-rpoC(M19) | S1017R, L1236T |
| KCCM11016P-rpoC(M20) | G1230Y, N1260H |

Example 5: Construction of Vector for Insertion of the rpoC Mutant into Chromosome of the Strain Producing High-Concentration of L-Lysine To examine the effects of mutations in a region showing a high homology to G and H domains of *E. coli* rpoC, among the mutations in the sequence-substituted rpoC mutant strains which were confirmed in Example 2, vectors for chromosomal insertion thereof were constructed.

Based on the reported base sequences, primers of SEQ ID NOS: 28 and 30 having an EcoRI restriction site at the 5'-terminal and a primer of SEQ ID NO: 30 having a SalI restriction site at the 3'-terminal were synthesized. Of them, primers of SEQ ID NOS: 28 and 30, and M1, M2, M4, M7, M8, M13, M16, M17, M18, and M19 of KCCM11016P-rpoC, namely, 10 kinds of chromosomes as templates, were used to amplify about 2000 bp of 10 kinds of rpoC(mt) gene fragments by PCR. PCR conditions consisted of denaturation at 94° C. for 5 minutes, 30 cycles of denaturation at 94° C. for 30 seconds, annealing at 56° C. for 30 seconds, and polymerization at 72° C. for 2 minutes, and then denaturation at 72° C. for 7 minutes. Further, primers of SEQ ID NOS: 29 and 30, and M3, M5, M6, M9, M10, M11, M12, M14, M15, and M20 of KCCM11016P-rpoC, namely, 10 kinds of chromosomes as templates, were used to amplify about 600 bp of 10 kinds of rpoC(mt) gene fragments by PCR. Primers used herein are represented by SEQ ID NOS: 28 to 30.

20 kinds of gene fragments amplified by PCR were treated with restriction enzymes, EcoRI and SalI, respectively to obtain DNA fragments, each thereof was ligated to a pDZ vector (Korean Patent NO. 2009-0094433) for chromosomal insertion having EcoRI and SalI restriction sites, and transformed into *E. coli* DH5a, which was spread on an LB solid medium containing kanamycin (25 mg/l). Colonies transformed with the desired gene-inserted vector were selected by PCR, and plasmids were obtained therefrom by a generally known plasmid extraction method, and these plasmids were designated as pDZ-rpoC(M1)~(M20) according to the number of the strain used as a template, respectively.

Example 6: Introduction of rpoC Mutant into Chromosome of the KCCM11016P Strain Producing High-Concentration of L-Lysine and Comparison of Lysine Productivity pDZ-rpoC(M1)~(M20) vectors prepared in Example 5 were transformed to an L-lysine-producing strain, *Corynebacterium glutamicum* KCCM11016P by homologous chromosome recombination. Thereafter, the strains having chromosomal insertion of rpoC mutation were selected by sequencing analysis, and cultured in the same manner as in Example 3. Concentrations of L-lysine therein were analyzed, and the results are given in Table 3. The strains introduced with rpoC mutations were designated as *Corynebacterium glutamicum* KCCM11016P::rpoC(M1)~(M20), respectively.

TABLE 3

| | | L-lysine (g/l) | | | |
|---|---|---|---|---|---|
| | Strain | Batch 1 | Batch 2 | Batch 3 | Average |
| Control group | KCCM11016P | 42.2 | 43.4 | 42.7 | 42.8 |
| 1 | KCCM11016P::rpoC(M1) | 45.2 | 45.2 | 44.9 | 45.1 |
| 2 | KCCM11016P::rpoC(M2) | 46.2 | 45.8 | 46.5 | 46.2 |
| 3 | KCCM11016P::rpoC(M3) | 47 | 47.9 | 47.5 | 47.5 |
| 4 | KCCM11016P::rpoC(M4) | 47.6 | 47.2 | 47.8 | 47.5 |
| 5 | KCCM11016P::rpoC(M5) | 48.3 | 49.8 | 49.5 | 49.2 |
| 6 | KCCM11016P::rpoC(M6) | 46.3 | 46.5 | 46 | 46.3 |
| 7 | KCCM11016P::rpoC(M7) | 45.8 | 44.7 | 45.2 | 45.2 |
| 8 | KCCM11016P::rpoC(M8) | 46.1 | 46.5 | 45.1 | 45.9 |
| 9 | KCCM11016P::rpoC(M9) | 45.9 | 46.8 | 47.1 | 46.6 |
| 10 | KCCM11016P::rpoC(M10) | 47.2 | 47.6 | 47.4 | 47.4 |
| 11 | KCCM11016P::rpoC(M11) | 45.3 | 45.8 | 45.9 | 45.7 |
| 12 | KCCM11016P::rpoC(M12) | 47.8 | 47.8 | 48.2 | 47.9 |
| 13 | KCCM11016P::rpoC(M13) | 46.3 | 46 | 46.6 | 46.3 |
| 14 | KCCM11016P::rpoC(M14) | 47.2 | 46.9 | 46.7 | 46.9 |
| 15 | KCCM11016P::rpoC(M15) | 50.1 | 48.7 | 49.2 | 49.3 |
| 16 | KCCM11016P::rpoC(M16) | 46.2 | 45.9 | 45.8 | 46 |
| 17 | KCCM11016P::rpoC(M17) | 45.3 | 45.8 | 45.9 | 45.7 |
| 18 | KCCM11016P::rpoC(M18) | 47.8 | 47.6 | 47.2 | 47.5 |
| 19 | KCCM11016P::rpoC(M19) | 46.8 | 46.3 | 45.9 | 46.3 |
| 20 | KCCM11016P::rpoC(M20) | 47.6 | 47.3 | 47.8 | 47.6 |

As shown in Table 3, average concentrations of L-lysine were increased as high as about 6~15% in KCCM11016P::rpoC(M1)~(M20), each was introduced with an rpoC gene having a substitution of 1 or 2 base(s), compared to a control group, KCCM11016P having a wild-type rpoC gene. Among them, KCCM11016P::rpoC(M15) as a representative of the top 20%, KCCM11016P::rpoC(M10) as a representative of the top 40%, and KCCM11016P::rpoC(M19) as a representative of the top 60% were named CA01-2267, CA01-2268, and CA01-2266, respectively and deposited at the Korean Culture Center of Microorganisms (KCCM) on Jun. 12, 2013 with Accession NOs: KCCM11428P, KCCM11429P, and KCCM11427P.

Example 7: Introduction of rpoC Mutant into Chromosome of the KCCM11347P Strain Producing High-Concentration of L-Lysine and Comparison of Lysine Productivity To examine the effects in other strains belonging to the genus *Corynebacterium glutamicum*, strains were prepared by introducing rpoC mutations into an L-lysine-producing strain *Corynebacterium glutamicum* KCCM11347P (Korean Patent No. 1994-0001307, international deposited microorganism of KFCC10750) in the same manner as in Example 6, and designated as KCCM11347P::rpoC(M1)~(M20), respectively. They were cultured in the same manner as in Example 3, and concentrations of L-lysine therein were analyzed, and the results are given in Table 4.

TABLE 4

Concentrations of L-lysine produced by KFCC10750::rpoC(M1)~(M20)

| | | L-lysine (g/l) | | | |
|---|---|---|---|---|---|
| | Strain | Batch 1 | Batch 2 | Batch 3 | Average |
| Control group | KCCM11347P | 38.3 | 38 | 38.5 | 38.3 |
| 1 | KCCM11347P::rpoC(M1) | 41.2 | 41.3 | 41.8 | 41.6 |
| 2 | KCCM11347P::rpoC(M2) | 42.8 | 42.2 | 42.7 | 42.5 |
| 3 | KCCM11347P::rpoC(M3) | 42.7 | 43.7 | 43.8 | 43.8 |
| 4 | KCCM11347P::rpoC(M4) | 43.6 | 45.5 | 41.9 | 43.7 |
| 5 | KCCM11347P::rpoC(M5) | 44.2 | 44.8 | 44.6 | 44.5 |
| 6 | KCCM11347P::rpoC(M6) | 42.3 | 42 | 42.8 | 42.4 |
| 7 | KCCM11347P::rpoC(M7) | 42.1 | 42.3 | 42 | 42.2 |
| 8 | KCCM11347P::rpoC(M8) | 42.2 | 42.6 | 42.8 | 42.5 |
| 9 | KCCM11347P::rpoC(M9) | 41.8 | 42.9 | 43 | 43 |
| 10 | KCCM11347P::rpoC(M10) | 43.7 | 43 | 42.8 | 43.2 |
| 11 | KCCM11347P::rpoC(M11) | 42.2 | 42.7 | 41.8 | 42.3 |
| 12 | KCCM11347P::rpoC(M12) | 43.8 | 43.9 | 44 | 43.9 |
| 13 | KCCM11347P::rpoC(M13) | 43.3 | 43.3 | 41.3 | 42.6 |
| 14 | KCCM11347P::rpoC(M14) | 42.4 | 42.2 | 43.8 | 43 |
| 15 | KCCM11347P::rpoC(M15) | 44 | 44.8 | 44.2 | 44.5 |
| 16 | KCCM11347P::rpoC(M16) | 43 | 42.8 | 42.3 | 42.6 |
| 17 | KCCM11347P::rpoC(M17) | 40.8 | 43.3 | 41.8 | 42.6 |
| 18 | KCCM11347P::rpoC(M18) | 43 | 42.7 | 43.5 | 43.1 |
| 19 | KCCM11347P::rpoC(M19) | 42.8 | 42.7 | 43 | 42.8 |
| 20 | KCCM11347P::rpoC(M20) | 44.1 | 44.4 | 44.4 | 44.3 |

As shown in Table 4, it was found that the average concentrations of L-lysine were increased by 8~16% in experimental groups 1~20, namely, KCCM11347P::rpoC(M1)~(M20), each was introduced with an rpoC gene having a substitution of 1 or 2 base(s), compared to a control group, KCCM11347P having a wild-type rpoC gene.

Example 8: Introduction of rpoC Mutant into Chromosome of the KCCM10770P Strain Producing High-Concentration of L-Lysine and Comparison of Lysine Productivity To examine the effects in other strains belonging to the genus *Corynebacterium glutamicum*, strains were prepared by introducing rpoC mutations into an L-lysine-producing strain *Corynebacterium glutamicum* KCCM10770P (Korean Patent No. 0924065) in the same manner as in Example 6, and designated as KCCM10770P::rpoC(M1)~(M20), respectively. The KCCM10770P strain is an L-lysine-producing strain derived from KCCM11016P, which retains one or more copies of 6 types of the genes constituting the lysine biosynthesis pathway, namely, aspB (aspartate aminotransferase-encoding gene), lysC (aspartate kinase-encoding gene), asd (aspartate semialdehyde dehydrogenase-encoding gene), dapA (dihydrodipicolinate synthase-encoding gene), dapB (dihydrodipicolinate reductase-encoding gene) and lysA (diaminopimelate decarboxylate-encoding gene) on the chromosome. They were cultured in the same manner as in Example 3, and concentrations of L-lysine therein were analyzed, and the results are given in Table 5.

TABLE 5

Concentrations of L-lysine produced by KCCM10770P::rpoC(M1)~(M20)

| | Strain | L-lysine (g/l) | | | |
|---|---|---|---|---|---|
| | | Batch 1 | Batch 2 | Batch 3 | Average |
| Control group | KCCM10770P | 47.8 | 47.2 | 47.5 | 47.5 |
| 1 | KCCM10770P::rpoC(M1) | 50.2 | 50 | 48.9 | 49.7 |
| 2 | KCCM10770P::rpoC(M2) | 50.2 | 50.8 | 50.9 | 50.6 |
| 3 | KCCM10770P::rpoC(M3) | 51.8 | 51.8 | 51.2 | 51.6 |
| 4 | KCCM10770P::rpoC(M4) | 51.8 | 51.6 | 51.2 | 51.5 |
| 5 | KCCM10770P::rpoC(M5) | 52 | 52.3 | 52.6 | 52.3 |
| 6 | KCCM10770P::rpoC(M6) | 50.7 | 50.4 | 50.4 | 50.5 |
| 7 | KCCM10770P::rpoC(M7) | 49.2 | 49.8 | 49.5 | 49.5 |
| 8 | KCCM10770P::rpoC(M8) | 50.2 | 50.4 | 50.7 | 50.4 |
| 9 | KCCM10770P::rpoC(M9) | 51.4 | 51 | 51.4 | 51.3 |
| 10 | KCCM10770P::rpoC(M10) | 51.6 | 51.3 | 50.9 | 51.3 |
| 11 | KCCM10770P::rpoC(M11) | 49.2 | 49 | 48 | 48.7 |
| 12 | KCCM10770P::rpoC(M12) | 52 | 51.8 | 52.1 | 52 |
| 13 | KCCM10770P::rpoC(M13) | 51.2 | 51.8 | 51 | 51.3 |
| 14 | KCCM10770P::rpoC(M14) | 52.2 | 49.9 | 51.8 | 51.3 |
| 15 | KCCM10770P::rpoC(M15) | 52.6 | 51.8 | 52.3 | 52.2 |
| 16 | KCCM10770P::rpoC(M16) | 50.2 | 50.6 | 50.4 | 50.4 |
| 17 | KCCM10770P::rpoC(M17) | 49.8 | 49.8 | 49.7 | 49.8 |
| 18 | KCCM10770P::rpoC(M18) | 51 | 51.2 | 52.1 | 51.4 |
| 19 | KCCM10770P::rpoC(M19) | 50.2 | 51.6 | 50.8 | 50.9 |
| 20 | KCCM10770P::rpoC(M20) | 51.8 | 51.8 | 51.8 | 51.8 |

As shown in Table 5, it was found that the average concentrations of L-lysine were increased by about 3~10% in experimental groups 1~20, namely, KCCM10770P::rpoC (M1)~(M20), each was introduced with an rpoC gene having a substitution of 1 or 2 base(s), compared to a control group, KCCM10770P having a wild-type rpoC gene.

Example 9: Introduction of rpoC Mutant into Chromosome of the CJ3P Strain Producing High-Concentration of L-Lysine and Comparison of Lysine Productivity To examine the effects in other strains belonging to the genus *Corynebacterium glutamicum*, strains were prepared by introducing rpoC mutations into an L-lysine-producing strain CJ3P (Binder et al. Genome Biology 2012, 13:R40) in the same manner as in Example 6, and designated as CJ3P::rpoC(M1)~(M20), respectively. The CJ3P strain is a *Corynebacterium glutamicum* strain having L-lysine productivity, which is prepared by introducing 3 types of mutations (pyc(Pro458Ser), hom(Val59Ala), lysC (Thr311Ile)) into a wild-type by a known technique. They were cultured in the same manner as in Example 3, and concentrations of L-lysine therein were analyzed, and the results are given in Table 6.

TABLE 6

Concentration of L-lysine produced by CJ3P::rpoC(M1)~(M20)

| | Strain | L-lysine (g/l) | | | |
|---|---|---|---|---|---|
| | | Batch 1 | Batch 2 | Batch 3 | Average |
| Control group | CJ3P | 8.3 | 8 | 8.4 | 8.2 |
| 1 | CJ3P::rpoC(M1) | 8.9 | 9.1 | 9.3 | 9.1 |
| 2 | CJ3P::rpoC(M2) | 10.8 | 10.1 | 9.7 | 10.2 |
| 3 | CJ3P::rpoC(M3) | 11.9 | 11.7 | 11.2 | 11.6 |
| 4 | CJ3P::rpoC(M4) | 11.8 | 11.9 | 11 | 11.6 |
| 5 | CJ3P::rpoC(M5) | 11.8 | 11.7 | 12 | 11.8 |
| 6 | CJ3P::rpoC(M6) | 10.2 | 10 | 10.3 | 10.2 |
| 7 | CJ3P::rpoC(M7) | 8.9 | 8.7 | 9.1 | 8.9 |
| 8 | CJ3P::rpoC(M8) | 9.7 | 9.7 | 9.8 | 9.7 |
| 9 | CJ3P::rpoC(M9) | 11.2 | 11.3 | 11.1 | 11.2 |
| 10 | CJ3P::rpoC(M10) | 11.2 | 10.9 | 10.8 | 11 |
| 11 | CJ3P::rpoC(M11) | 9.2 | 9.5 | 8.7 | 9.1 |
| 12 | CJ3P::rpoC(M12) | 12.9 | 13 | 12.7 | 12.9 |
| 13 | CJ3P::rpoC(M13) | 10.8 | 10.3 | 10.3 | 10.5 |
| 14 | CJ3P::rpoC(M14) | 10.7 | 10.5 | 11 | 10.7 |
| 15 | CJ3P::rpoC(M15) | 12.4 | 12.2 | 12.3 | 12.3 |
| 16 | CJ3P::rpoC(M16) | 9.6 | 9.9 | 9.7 | 9.7 |
| 17 | CJ3P::rpoC(M17) | 8.9 | 9.8 | 9.4 | 9.4 |
| 18 | CJ3P::rpoC(M18) | 10.9 | 10.9 | 10.7 | 10.8 |
| 19 | CJ3P::rpoC(M19) | 10.3 | 10.3 | 10.5 | 10.4 |
| 20 | CJ3P::rpoC(M20) | 11.2 | 12 | 11.8 | 11.7 |

As shown in Table 6, it was found that the average concentrations of L-lysine were increased up to 57% in experimental groups 1~20, namely, CJ3P::rpoC (M1)~(M20), each was introduced with an rpoC gene having a substitution of 1 or 2 base(s), compared to a control group, CJ3P having a wild-type rpoC gene. Accordingly, lysine productivity is greatly enhanced by introducing mutations into the positions 975 to 1284, this region showing high homology to G and H domains of rpoC, which is an RNA polymerase beta prime subunit of *E. coli*.

The invention claimed is:

1. An RNA polymerase beta prime subunit (β'-subunit) mutant having an amino acid sequence, wherein the amino acid sequence is selected from the group consisting of SEQ ID NO: 8 to SEQ ID NO:27.

2. A polynucleotide having a nucleotide sequence encoding the RNA polymerase beta prime subunit mutant of claim 1.

3. A vector comprising the polynucleotide of claim 2 operably linked to a regulatory sequence.

4. A *Corynebacterium* microorganism expressing the RNA polymerase beta prime subunit mutant of claim 1.

5. The microorganism of claim 4, wherein the microorganism belonging to the genus *Corynebacterium* is *Corynebacterium glutamicum*.

6. A method of producing L-lysine, the method comprising the steps of:
   culturing the microorganism of claim 4 to produce L-lysine in a culture; and
   recovering L-lysine from the culture.

\* \* \* \* \*

SEQUENCE LISTING

<160> NUMBER OF SEQ ID NOS: 30

<210> SEQ ID NO 1
<211> LENGTH: 1333
<212> TYPE: PRT
<213> ORGANISM: Corynebacterium

<400> SEQUENCE: 1

Met Leu Asp Val Asn Val Phe Asp Glu Leu Arg Ile Gly Leu Ala Thr

```
            1               5              10              15
        Ala Asp Asp Ile Arg Arg Trp Ser Lys Gly Glu Val Lys Lys Pro Glu
                         20              25              30

Thr Ile Asn Tyr Arg Thr Leu Lys Pro Glu Lys Asp Gly Leu Phe Cys
                         35              40              45

Glu Arg Ile Phe Gly Pro Thr Arg Asp Trp Glu Cys Ala Cys Gly Lys
                 50              55              60

Tyr Lys Arg Val Arg Tyr Lys Gly Ile Ile Cys Glu Arg Cys Gly Val
         65              70              75              80

Glu Val Thr Lys Ser Lys Val Arg Arg Glu Arg Met Gly His Ile Glu
                         85              90              95

Leu Ala Ala Pro Val Thr His Ile Trp Tyr Phe Lys Gly Val Pro Ser
                        100             105             110

Arg Leu Gly Tyr Leu Leu Asp Leu Ala Pro Lys Asp Leu Asp Leu Ile
                        115             120             125

Ile Tyr Phe Gly Ala Asn Ile Ile Thr Ser Val Asp Glu Glu Ala Arg
                        130             135             140

His Ser Asp Gln Thr Thr Leu Glu Ala Glu Met Leu Leu Glu Lys Lys
        145             150             155             160

Asp Val Glu Ala Asp Ala Glu Ser Asp Ile Ala Glu Arg Ala Glu Lys
                        165             170             175

Leu Glu Glu Asp Leu Ala Glu Leu Glu Ala Ala Gly Ala Lys Ala Asp
                        180             185             190

Ala Arg Arg Lys Val Gln Ala Ala Asp Lys Glu Met Gln His Ile
                        195             200             205

Arg Glu Arg Ala Gln Arg Glu Ile Asp Arg Leu Asp Glu Val Trp Gln
                        210             215             220

Thr Phe Ile Lys Leu Ala Pro Lys Gln Met Ile Arg Asp Glu Lys Leu
        225             230             235             240

Tyr Asp Glu Leu Ile Asp Arg Tyr Glu Asp Tyr Phe Thr Gly Gly Met
                        245             250             255

Gly Ala Glu Ser Ile Glu Ala Leu Ile Gln Asn Phe Asp Leu Asp Ala
                        260             265             270

Glu Ala Glu Glu Leu Arg Asp Ile Ile Asn Asn Gly Lys Gly Gln Lys
                        275             280             285

Lys Met Arg Ala Leu Lys Arg Leu Lys Val Val Ala Ala Phe Gln Arg
        290             295             300

Ser Gly Asn Asp Pro Ala Gly Met Val Leu Asn Ala Ile Pro Val Ile
        305             310             315             320

Pro Pro Glu Leu Arg Pro Met Val Gln Leu Asp Gly Gly Arg Phe Ala
                        325             330             335

Thr Ser Asp Leu Asn Asp Leu Tyr Arg Arg Val Ile Asn Arg Asn Asn
                        340             345             350

Arg Leu Lys Arg Met Ile Glu Leu Gly Ala Pro Glu Ile Ile Val Asn
                        355             360             365

Asn Glu Lys Arg Met Leu Gln Glu Ser Val Asp Ala Leu Phe Asp Asn
                        370             375             380

Gly Arg Arg Gly Arg Pro Val Thr Gly Pro Gly Asn Arg Pro Leu Lys
        385             390             395             400

Ser Leu Ser Asp Leu Leu Lys Gly Lys Gln Gly Arg Phe Arg Gln Asn
                        405             410             415

Leu Leu Gly Lys Arg Val Asp Tyr Ser Gly Arg Ser Val Ile Ile Val
                        420             425             430
```

```
Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
    610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
        675                 680                 685

Gly Val Met Val Arg Lys Gly Gly Ser Asp Lys Ile Met Leu Gly
    690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
        755                 760                 765

Lys Tyr Asn Arg Gly Lys Leu Thr Gly Arg Glu Arg Tyr Asp Arg Leu
    770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
        835                 840                 845
```

-continued

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
            885                 890                 895

Arg Val Glu Asp Cys Gly Thr Arg Gln Gly Val Arg Val Pro Val Ala
900                 905                 910

Ala Glu Val Leu Asp Ala Thr Gly Ala Val Thr Gly Tyr Thr Arg His
            915                 920                 925

Asp Leu Ile Glu Thr Ser Val Ser Gly Arg Val Leu Ala Gly Asp Ala
930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
            965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
            995                 1000                1005

Ala Val Gly Ile Val Ala Ala Gln Ser Ile Gly Glu Pro Gly Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
    1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
            1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
    1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
    1220                1225                1230

Lys Ala Ser Leu Ala Thr Glu Ser Trp Leu Ser Ala Ala Ser Phe Gln
            1235                1240                1245

Glu Thr Thr Arg Val Leu Thr Asp Ala Ala Ile Asn Lys Arg Ser Asp
    1250                1255                1260

Lys Leu Ile Gly Leu Lys Glu Asn Val Ile Ile Gly Lys Leu Ile Pro

-continued

```
1265                1270                1275                1280

Ala Gly Thr Gly Ile Ser Arg Tyr Arg Asn Ile Ser Ile Lys Pro Thr
                1285                1290                1295
Glu Ala Ala Arg Asn Ala Ala Tyr Ser Ile Pro Thr Tyr Gly Glu Ser
            1300                1305                1310
Ile Tyr Gly Asp Asp Gly Phe Gly Glu Phe Thr Gly Ala Ser Val Pro
        1315                1320                1325
Leu Asp Glu Ala Phe
    1330

<210> SEQ ID NO 2
<211> LENGTH: 60
<212> TYPE: PRT
<213> ORGANISM: G domain of Corynebacterium

<400> SEQUENCE: 2

Val Lys Val Arg Ser Val Leu Thr Cys Gln Thr Pro Thr Gly Val Cys
  1               5                   10                  15

Ala Lys Cys Tyr Gly Lys Ser Met Ala Ser Gly Gln Gln Val Asp Ile
            20                  25                  30

Gly Glu Ala Val Gly Ile Val Ala Ala Gln Ser Ile Gly Glu Pro Gly
        35                  40                  45

Thr Gln Leu Thr Met Arg Thr Phe His Gln Gly Gly
     50                  55                  60

<210> SEQ ID NO 3
<211> LENGTH: 55
<212> TYPE: PRT
<213> ORGANISM: H domain of Corynebacterium

<400> SEQUENCE: 3

Gly Ile Thr Lys Ala Ser Leu Ala Thr Glu Ser Trp Leu Ser Ala Ala
  1               5                   10                  15

Ser Phe Gln Glu Thr Thr Arg Val Leu Thr Asp Ala Ala Ile Asn Lys
            20                  25                  30

Arg Ser Asp Lys Leu Ile Gly Leu Lys Glu Asn Val Ile Ile Gly Lys
        35                  40                  45

Leu Ile Pro Ala Gly Thr Gly
     50                  55

<210> SEQ ID NO 4
<211> LENGTH: 1407
<212> TYPE: PRT
<213> ORGANISM: E.coli

<400> SEQUENCE: 4

Met Lys Asp Leu Leu Lys Phe Leu Lys Ala Gln Thr Lys Thr Glu Glu
  1               5                   10                  15

Phe Asp Ala Ile Lys Ile Ala Leu Ala Ser Pro Asp Met Ile Arg Ser
            20                  25                  30

Trp Ser Phe Gly Glu Val Lys Lys Pro Glu Thr Ile Asn Tyr Arg Thr
        35                  40                  45

Phe Lys Pro Glu Arg Asp Gly Leu Phe Cys Ala Arg Ile Phe Gly Pro
     50                  55                  60

Val Lys Asp Tyr Glu Cys Leu Cys Gly Lys Tyr Lys Arg Leu Lys His
 65                  70                  75                  80

Arg Gly Val Ile Cys Glu Lys Cys Gly Val Glu Val Thr Gln Thr Lys
                 85                  90                  95
```

```
Val Arg Arg Glu Arg Met Gly His Ile Glu Leu Ala Ser Pro Thr Ala
            100                 105                 110
His Ile Trp Phe Leu Lys Ser Leu Pro Ser Arg Ile Gly Leu Leu Leu
            115                 120                 125
Asp Met Pro Leu Arg Asp Ile Glu Arg Val Leu Tyr Phe Glu Ser Tyr
            130                 135                 140
Val Val Ile Glu Gly Gly Met Thr Asn Leu Glu Arg Gln Gln Ile Leu
145                 150                 155                 160
Thr Glu Glu Gln Tyr Leu Asp Ala Leu Glu Glu Phe Gly Asp Glu Phe
                165                 170                 175
Asp Ala Lys Met Gly Ala Glu Ala Ile Gln Ala Leu Leu Lys Ser Met
                180                 185                 190
Asp Leu Glu Gln Glu Cys Glu Gln Leu Arg Glu Glu Leu Asn Glu Thr
                195                 200                 205
Asn Ser Glu Thr Lys Arg Lys Leu Thr Lys Arg Ile Lys Leu Leu
            210                 215                 220
Glu Ala Phe Val Gln Ser Gly Asn Lys Pro Glu Trp Met Ile Leu Thr
225                 230                 235                 240
Val Leu Pro Val Leu Pro Pro Asp Leu Arg Pro Leu Val Pro Leu Asp
                245                 250                 255
Gly Gly Arg Phe Ala Thr Ser Asp Leu Asn Asp Leu Tyr Arg Arg Val
                260                 265                 270
Ile Asn Arg Asn Asn Arg Leu Lys Arg Leu Leu Asp Leu Ala Ala Pro
            275                 280                 285
Asp Ile Ile Val Arg Asn Glu Lys Arg Met Leu Gln Glu Ala Val Asp
            290                 295                 300
Ala Leu Leu Asp Asn Gly Arg Arg Gly Arg Ala Ile Thr Gly Ser Asn
305                 310                 315                 320
Lys Arg Pro Leu Lys Ser Leu Ala Asp Met Ile Lys Gly Lys Gln Gly
                325                 330                 335
Arg Phe Arg Gln Asn Leu Leu Gly Lys Arg Val Asp Tyr Ser Gly Arg
                340                 345                 350
Ser Val Ile Thr Val Gly Pro Tyr Leu Arg Leu His Gln Cys Gly Leu
            355                 360                 365
Pro Lys Lys Met Ala Leu Glu Leu Phe Lys Pro Phe Ile Tyr Gly Lys
            370                 375                 380
Leu Glu Leu Arg Gly Leu Ala Thr Thr Ile Lys Ala Ala Lys Lys Met
385                 390                 395                 400
Val Glu Arg Glu Glu Ala Val Val Trp Asp Ile Leu Asp Glu Val Ile
                405                 410                 415
Arg Glu His Pro Val Leu Leu Asn Arg Ala Pro Thr Leu His Arg Leu
                420                 425                 430
Gly Ile Gln Ala Phe Glu Pro Val Leu Ile Glu Gly Lys Ala Ile Gln
            435                 440                 445
Leu His Pro Leu Val Cys Ala Ala Tyr Asn Ala Asp Phe Asp Gly Asp
            450                 455                 460
Gln Met Ala Val His Val Pro Leu Thr Leu Glu Ala Gln Leu Glu Ala
465                 470                 475                 480
Arg Ala Leu Met Met Ser Thr Asn Asn Ile Leu Ser Pro Ala Asn Gly
                485                 490                 495
Glu Pro Ile Ile Val Pro Ser Gln Asp Val Val Leu Gly Leu Tyr Tyr
            500                 505                 510
```

-continued

```
Met Thr Arg Asp Cys Val Asn Ala Lys Gly Glu Gly Met Val Leu Thr
            515                 520                 525

Gly Pro Lys Glu Ala Glu Arg Leu Tyr Arg Ser Gly Leu Ala Ser Leu
    530                 535                 540

His Ala Arg Val Lys Val Arg Ile Thr Glu Tyr Glu Lys Asp Ala Asn
545                 550                 555                 560

Gly Glu Leu Val Ala Lys Thr Ser Leu Lys Asp Thr Thr Val Gly Arg
                565                 570                 575

Ala Ile Leu Trp Met Ile Val Pro Lys Gly Leu Pro Tyr Ser Ile Val
            580                 585                 590

Asn Gln Ala Leu Gly Lys Lys Ala Ile Ser Lys Met Leu Asn Thr Cys
        595                 600                 605

Tyr Arg Ile Leu Gly Leu Lys Pro Thr Val Ile Phe Ala Asp Gln Ile
    610                 615                 620

Met Tyr Thr Gly Phe Ala Tyr Ala Ala Arg Ser Gly Ala Ser Val Gly
625                 630                 635                 640

Ile Asp Asp Met Val Ile Pro Glu Lys Lys His Glu Ile Ile Ser Glu
                645                 650                 655

Ala Glu Ala Glu Val Ala Glu Ile Gln Glu Gln Phe Gln Ser Gly Leu
            660                 665                 670

Val Thr Ala Gly Glu Arg Tyr Asn Lys Val Ile Asp Ile Trp Ala Ala
        675                 680                 685

Ala Asn Asp Arg Val Ser Lys Ala Met Met Asp Asn Leu Gln Thr Glu
    690                 695                 700

Thr Val Ile Asn Arg Asp Gly Gln Glu Glu Lys Gln Val Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
        755                 760                 765

Val Leu Gln Tyr Phe Ile Ser Thr His Gly Ala Arg Lys Gly Leu Ala
    770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Cys Gly Thr
                805                 810                 815

His Glu Gly Ile Met Met Thr Pro Val Ile Glu Gly Gly Asp Val Lys
            820                 825                 830

Glu Pro Leu Arg Asp Arg Val Leu Gly Arg Val Thr Ala Glu Asp Val
        835                 840                 845

Leu Lys Pro Gly Thr Ala Asp Ile Leu Val Pro Arg Asn Thr Leu Leu
    850                 855                 860

His Glu Gln Trp Cys Asp Leu Leu Glu Glu Asn Ser Val Asp Ala Val
865                 870                 875                 880

Lys Val Arg Ser Val Val Ser Cys Asp Thr Asp Phe Gly Val Cys Ala
                885                 890                 895

His Cys Tyr Gly Arg Asp Leu Ala Arg Gly His Ile Ile Asn Lys Gly
            900                 905                 910

Glu Ala Ile Gly Val Ile Ala Ala Gln Ser Ile Gly Glu Pro Gly Thr
        915                 920                 925

Gln Leu Thr Met Arg Thr Phe His Ile Gly Gly Ala Ala Ser Arg Ala
```

```
                930              935              940
Ala Ala Glu Ser Ser Ile Gln Val Lys Asn Lys Gly Ser Ile Lys Leu
945                  950                  955                  960

Ser Asn Val Lys Ser Val Val Asn Ser Ser Gly Lys Leu Val Ile Thr
                965                  970                  975

Ser Arg Asn Thr Glu Leu Lys Leu Ile Asp Glu Phe Gly Arg Thr Lys
                980                  985                  990

Glu Ser Tyr Lys Val Pro Tyr Gly Ala Val Leu Ala Lys Gly Asp Gly
                995                  1000                 1005

Glu Gln Val Ala Gly Gly Glu Thr Val Ala Asn Trp Asp Pro His Thr
    1010                 1015                 1020

Met Pro Val Ile Thr Glu Val Ser Gly Phe Val Arg Phe Thr Asp Met
1025                 1030                 1035                 1040

Ile Asp Gly Gln Thr Ile Thr Arg Gln Thr Asp Glu Leu Thr Gly Leu
                1045                 1050                 1055

Ser Ser Leu Val Val Leu Asp Ser Ala Glu Arg Thr Ala Gly Gly Lys
                1060                 1065                 1070

Asp Leu Arg Pro Ala Leu Lys Ile Val Asp Ala Gln Gly Asn Asp Val
    1075                 1080                 1085

Leu Ile Pro Gly Thr Asp Met Pro Ala Gln Tyr Phe Leu Pro Gly Lys
    1090                 1095                 1100

Ala Ile Val Gln Leu Glu Asp Gly Val Gln Ile Ser Ser Gly Asp Thr
1105                 1110                 1115                 1120

Leu Ala Arg Ile Pro Gln Glu Ser Gly Gly Thr Lys Asp Ile Thr Gly
                1125                 1130                 1135

Gly Leu Pro Arg Val Ala Asp Leu Phe Glu Ala Arg Arg Pro Lys Glu
                1140                 1145                 1150

Pro Ala Ile Leu Ala Glu Ile Ser Gly Ile Val Ser Phe Gly Lys Glu
                1155                 1160                 1165

Thr Lys Gly Lys Arg Arg Leu Val Ile Thr Pro Val Asp Gly Ser Asp
    1170                 1175                 1180

Pro Tyr Glu Glu Met Ile Pro Lys Trp Arg Gln Leu Asn Val Phe Glu
1185                 1190                 1195                 1200

Gly Glu Arg Val Glu Arg Gly Asp Val Ile Ser Asp Gly Pro Glu Ala
                1205                 1210                 1215

Pro His Asp Ile Leu Arg Leu Arg Gly Val His Ala Val Thr Arg Tyr
                1220                 1225                 1230

Ile Val Asn Glu Val Gln Asp Val Tyr Arg Leu Gln Gly Val Lys Ile
                1235                 1240                 1245

Asn Asp Lys His Ile Glu Val Ile Val Arg Gln Met Leu Arg Lys Ala
    1250                 1255                 1260

Thr Ile Val Asn Ala Gly Ser Ser Asp Phe Leu Glu Gly Glu Gln Val
1265                 1270                 1275                 1280

Glu Tyr Ser Arg Val Lys Ile Ala Asn Arg Glu Leu Glu Ala Asn Gly
                1285                 1290                 1295

Lys Val Gly Ala Thr Tyr Ser Arg Asp Leu Leu Gly Ile Thr Lys Ala
                1300                 1305                 1310

Ser Leu Ala Thr Glu Ser Phe Ile Ser Ala Ala Ser Phe Gln Glu Thr
                1315                 1320                 1325

Thr Arg Val Leu Thr Glu Ala Ala Val Ala Gly Lys Arg Asp Glu Leu
    1330                 1335                 1340

Arg Gly Leu Lys Glu Asn Val Ile Val Gly Arg Leu Ile Pro Ala Gly
1345                 1350                 1355                 1360
```

Thr Gly Tyr Ala Tyr His Gln Asp Arg Met Arg Arg Ala Ala Gly
            1365                1370                1375

Glu Ala Pro Ala Ala Pro Gln Val Thr Ala Glu Asp Ala Ser Ala Ser
        1380                1385                1390

Leu Ala Glu Leu Leu Asn Ala Gly Leu Gly Gly Ser Asp Asn Glu
        1395                1400            1405

<210> SEQ ID NO 5
<211> LENGTH: 3999
<212> TYPE: DNA
<213> ORGANISM: Corynebacterium

<400> SEQUENCE: 5

| | | | | | |
|---|---|---|---|---|---|
| gtgctcgacg | taaacgtctt | cgatgagctc | cgcatcggcc | tggccaccgc | cgacgacatc | 60 |
| cgccgttggt | ccaagggtga | ggtcaagaag | ccggagacca | tcaactaccg | aaccctcaag | 120 |
| cctgagaagg | acgtctgtt | ctgcgagcgt | atcttcggtc | caactcgcga | ctggagtgc | 180 |
| gcctgcggta | agtacaagcg | tgtccgctac | aagggcatca | tctgtgaacg | ctgtggcgtt | 240 |
| gaggtcacca | gtccaaggt | gcgccgtgag | cgcatgggac | acattgagct | cgctgcacca | 300 |
| gtaacccaca | tttggtactt | caagggcgtt | ccatcacgcc | tcggctacct | tttggacctt | 360 |
| gctccaaagg | acctggacct | catcatctac | ttcggtgcga | acatcatcac | cagcgtggac | 420 |
| gaagaggctc | gccacagcga | ccagaccact | cttgaggcag | aaatgcttct | ggagaagaag | 480 |
| gacgttgagg | cagacgcaga | gtctgacatt | gctgagcgtg | ctgaaaagct | cgaagaggat | 540 |
| cttgctgaac | ttgaggcagc | tggcgctaag | gccgacgctc | gccgcaaggt | tcaggctgct | 600 |
| gccgataagg | aaatgcagca | catccgtgag | cgtgcacagc | gcgaaatcga | tcgtctcgat | 660 |
| gaggtctggc | agaccttcat | caagcttgct | ccaaagcaga | tgatccgcga | tgagaagctc | 720 |
| tacgatgaac | tgatcgaccg | ctacgaggat | tacttcaccg | gtggtatggg | tgcagagtcc | 780 |
| attgaggctt | tgatccagaa | cttcgacctt | gatgctgagg | ctgaagagct | cgcgacatc | 840 |
| atcaacaatg | caagggcca | agaagaagatg | cgtgcactga | agcgcctgaa | ggttgttgca | 900 |
| gccttccagc | gttccggcaa | cgatcctgcc | ggcatggttt | tgaacgcgat | cccagtgatc | 960 |
| ccaccagagc | ttcgcccaat | ggttcagctt | gacggtggtc | gcttcgctac | ctccgacttg | 1020 |
| aacgaccttt | accgtcgtgt | gatcaaccgc | aacaaccgtc | tgaagcgcat | gattgagctc | 1080 |
| ggtgcacctg | agatcatcgt | gaacaacgag | aagcgcatgc | tgcaggaatc | tgtggacgcg | 1140 |
| ctgttcgaca | acggtcgtcg | tggtcgccca | gttaccggac | cgggtaaccg | tccgctgaag | 1200 |
| tctctgtctg | acttgctcaa | gggcaagcaa | ggccgtttcc | gtcagaacct | tctgggtaag | 1260 |
| cgtgttgact | actctggtcg | ttccgtaatt | atcgttggtc | ctcagctgcg | cctccacgaa | 1320 |
| tgtggtctgc | ctaagctgat | ggctctcgag | ctcttcaagc | ctttcgtcat | gaagcgcttg | 1380 |
| gtggagaacg | agtacgcaca | gaacatcaag | tctgcaaagc | gcatggttga | gcgtcagcgc | 1440 |
| cctgaggtgt | gggacgtcct | cgaagaggcc | atctctgagc | acccagtgat | gctgaaccgt | 1500 |
| gcaccaaccc | tgcaccgctt | gggcattcag | gctttcgagc | ctgtccttgt | tgagggtaag | 1560 |
| gctattcagc | tgcacccact | tgcttgtgaa | gctttcaacg | ccgacttcga | tggtgaccag | 1620 |
| atggcagttc | acctgccgct | gtccgctgaa | gctcaggctg | aggctcgcgt | gctgatgctt | 1680 |
| gcatccaaca | acattttgtc | cccagcttcc | ggtaagccgtt | tggctatgcc | tcgtctggat | 1740 |
| atggtgaccg | tctgtactaa | cctgactctg | gagaagtctt | ccgaggagtt | cggtggacag | 1800 |
| ggcgcttacc | agcctgcaga | tgaaaacggt | cctgaaaagg | gcgtgtattc | ctcactggca | 1860 |

```
gaagcaatca tggcttatga ccgtggtgta cttggcctgc aggcccagt tcgcatccgt    1920 ttgaaccacc tgcgcccacc agctgaggta gaagcagagc agttcccaga tggatggaac    1980
cagggcgaga cttggttggc tcacaccacc ttgggtcgcg ttatgttcaa cgagatcctg    2040
ccttggaact acccataact tgagggcgtt atggtccgta agggtggcgg ctccgacaag    2100
atcatgcttg gcgacgtagt caatgacctc gctgctaagt acccaatgat caccgtggct    2160
cagaccatgg acaagatgaa ggatgctggc ttctactggt caacccgttc cggtgtgacc    2220
atcgctatgt ctgacgtttt ggttcttcct aacaaggaag aaatgctgga ccgctacgag    2280
gaatctgcac gccagatcga agttaagtac aaccgcggta agctcaccgg ccgtgagcgc    2340
tacgaccgtc tggtcgagct gtggaaggac gcaactgacg aggttggaca ggctgtcgag    2400
gatctgtacc cagacgacaa cccaattcca atgatcgtga agtctggtgc tgccggtaac    2460
atgcgtcaga tctggaccct tgctggtatg aagggcatgg ttgtgaactc gaagggtgac    2520
tacatcaccc gcccgatcaa gacttccttc cgtgaaggct tgaccgttct cgagtacttc    2580
aacaactccc acggttcccg taagggcctg gccgataccg cgctgcgtac cgctgactcc    2640
ggttacctga cccgtcgtct tgttgacgtc gctcaggacg tcatcgtgcg tgttgaggac    2700
tgtggcaccc gccagggtgt tcgcgttcct gtcgctgctg aggttctgga tgcaactggt    2760
gctgtcaccg gctacacccg ccatgacctg atcgagactt ctgtctccgg tcgtgttctg    2820
gctggcgatg caaccaacgc tgcaggcgag gttgtgcttg ctgctggtac cgacctgacc    2880
gagctcaaca ttgaccttct ggtcgaggct ggcatcaagg acgtcaaggt tcgttccgta    2940
cttacctgcc agaccccaac cggtgttgt gctaagtgct acggcaagtc catggcttcc    3000
ggccagcagg ttgatatcgg agaggctgtc ggtattgttg ctgcacagtc cattggtgag    3060
cctggtaccc agctgaccat gcgtaccttc caccagggtg gtgtcggtgg cgatattacc    3120
ggcggtctgc ctcgtgttca ggagctgttt gaggcacgtg ttcctaagaa ctgtgcacca    3180
attgcttctg ttgaaggtgt tatccacctt gaggatgaag gcaacttcta cactctgacc    3240
atcgttcctg acgatggctc cgacaacgtt gtctacgaga agctgtccaa gcgacagggt    3300
cttgcatcca ctcgcgtggc tatggagtcc aacgctggtg cgttcattga gcgcaccttg    3360
accgaaggtg accgcgtcac cgttggtcag cgtctgctcc gtggtgcagc tgatccacac    3420
gacgtgctcg agatcctcgg tcgccgtggt gtggagcagc acctcatcga tgaggtgcag    3480
gctgtttacc gtgcacaggg tgtggccatc cacgacaagc acatcgaaat catcattcgt    3540
cagatgctgc gtcgcggtac cgtcattgag tccggttcca ccgagttcct tcctggttct    3600
ttggttgacc tctctgaggc gaagctggct aactctgagg caatcggtgc gggcggtcag    3660
cctgcagagc tgcgttctga tcatgggt atcaccaagg cctctctcgc aactgagtct    3720
tggctgtctg cagcgtcctt ccaggagacc actcgtgtcc tgactgatgc tgctatcaac    3780
aagcgctccg ataagctcat cggcctgaag ggaacgctca tcggtaagct gatcccagct    3840
ggtactggta tttcccgtta ccgcaacatc tccatcaagc caaccgaggc tgctcgcaac    3900
gccgcatact cgatcccaac ttatggtgag tcgatttacg gtgacgatgg attcggtgag    3960
ttcaccggcg catccgtccc attggatgag gctttctag               3999
```

<210> SEQ ID NO 6
<211> LENGTH: 20
<212> TYPE: DNA
<213> ORGANISM: Artificial Sequence
<220> FEATURE:

<223> OTHER INFORMATION: primer

<400> SEQUENCE: 6
aattgtgaag ggcgagaaca                                                    20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cagggcctca acttctcagc                                                    20

<210> SEQ ID NO 8
<211> LENGTH: 1333
<212> TYPE: PRT
<213> ORGANISM: Artificial Sequence
<220> FEATURE:
<223> OTHER INFORMATION: RpoC of KCCM11016P-rpoC(M1)

<400> SEQUENCE: 8

```
Met Leu Asp Val Asn Val Phe Asp Glu Leu Arg Ile Gly Leu Ala Thr
  1               5                  10                  15

Ala Asp Asp Ile Arg Arg Trp Ser Lys Gly Glu Val Lys Lys Pro Glu
                 20                  25                  30

Thr Ile Asn Tyr Arg Thr Leu Lys Pro Glu Lys Asp Gly Leu Phe Cys
             35                  40                  45

Glu Arg Ile Phe Gly Pro Thr Arg Asp Trp Glu Cys Ala Cys Gly Lys
         50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                 85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
            115                 120                 125

Ile Tyr Phe Gly Ala Asn Ile Ile Thr Ser Val Asp Glu Glu Ala Arg
        130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Gly Ala Lys Ala Asp
            180                 185                 190

Ala Arg Arg Lys Val Gln Ala Ala Asp Lys Glu Met Gln His Ile
            195                 200                 205

Arg Glu Arg Ala Gln Arg Glu Ile Asp Arg Leu Glu Val Trp Gln
            210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270
```

```
Glu Ala Glu Glu Leu Arg Asp Ile Ile Asn Asn Gly Lys Gly Gln Lys
            275                 280                 285

Lys Met Arg Ala Leu Lys Arg Leu Lys Val Val Ala Ala Phe Gln Arg
        290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Arg Phe Ala
                325                 330                 335

Thr Ser Asp Leu Asn Asp Leu Tyr Arg Val Ile Asn Arg Asn Asn
                340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
        420                 425                 430

Gly Pro Gln Leu Arg Leu His Glu Cys Gly Leu Pro Lys Leu Met Ala
                435                 440                 445

Leu Glu Leu Phe Lys Pro Phe Val Met Lys Arg Leu Val Glu Asn Glu
        450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
                500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
                580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
                660                 665                 670

Arg Val Met Phe Asn Glu Ile Leu Pro Trp Asn Tyr Pro Tyr Leu Glu
            675                 680                 685

Gly Val Met Val Arg Lys Gly Gly Gly Ser Asp Lys Ile Met Leu Gly
```

```
                690                 695                 700
Asp Val Val Asn Asp Leu Ala Ala Lys Tyr Pro Met Ile Thr Val Ala
705                 710                 715                 720
Gln Thr Met Asp Lys Met Lys Asp Ala Gly Phe Tyr Trp Ser Thr Arg
                725                 730                 735
Ser Gly Val Thr Ile Ala Met Ser Asp Val Leu Val Leu Pro Asn Lys
                740                 745                 750
Glu Glu Met Leu Asp Arg Tyr Glu Glu Ser Ala Arg Gln Ile Glu Val
                755                 760                 765
Lys Tyr Asn Arg Gly Lys Leu Thr Gly Arg Glu Arg Tyr Asp Arg Leu
                770                 775                 780
Val Glu Leu Trp Lys Asp Ala Thr Asp Glu Val Gly Gln Ala Val Glu
785                 790                 795                 800
Asp Leu Tyr Pro Asp Asp Asn Pro Ile Pro Met Ile Val Lys Ser Gly
                805                 810                 815
Ala Ala Gly Asn Met Arg Gln Ile Trp Thr Leu Ala Gly Met Lys Gly
                820                 825                 830
Met Val Val Asn Ser Lys Gly Asp Tyr Ile Thr Arg Pro Ile Lys Thr
                835                 840                 845
Ser Phe Arg Glu Gly Leu Thr Val Leu Glu Tyr Phe Asn Asn Ser His
                850                 855                 860
Gly Ser Arg Lys Gly Leu Ala Asp Thr Ala Leu Arg Thr Ala Asp Ser
865                 870                 875                 880
Gly Tyr Leu Thr Arg Arg Leu Val Asp Val Ala Gln Asp Val Ile Val
                885                 890                 895
Arg Val Glu Asp Cys Gly Thr Arg Gln Gly Val Arg Val Pro Val Ala
                900                 905                 910
Ala Glu Val Leu Asp Ala Thr Gly Ala Val Thr Gly Tyr Thr Arg His
                915                 920                 925
Asp Leu Ile Glu Thr Ser Val Ser Gly Arg Val Leu Ala Gly Asp Ala
                930                 935                 940
Thr Asn Ala Ala Gly Glu Val Val Leu Ala Ala Gly Thr Asp Leu Thr
945                 950                 955                 960
Glu Leu Asn Ile Asp Leu Leu Val Glu Ala Gly Ile Lys Asp Val Lys
                965                 970                 975
Val Arg Ser Val Leu Thr Cys Gln Thr Pro Thr Gly Val Cys Ala Lys
                980                 985                 990
Cys Tyr Gly Lys Ser Met Ala Ser Gly Gln Gln Val Asp Ile Gly Glu
                995                1000                1005
Ala Val Gly Ile Val Ala Ala Gly Ser Ile Gly Glu Pro Gly Thr Gln
   1010                1015                1020
Leu Thr Met Arg Thr Phe His Gln Gly Gly Val Gly Gly Asp Ile Thr
1025                1030                1035                1040
Gly Gly Leu Pro Arg Val Gln Glu Leu Phe Glu Ala Arg Val Pro Lys
                1045                1050                1055
Asn Cys Ala Pro Ile Ala Ser Val Glu Gly Val Ile His Leu Glu Asp
            1060                1065                1070
Glu Gly Asn Phe Tyr Thr Leu Thr Ile Val Pro Asp Asp Gly Ser Asp
            1075                1080                1085
Asn Val Val Tyr Glu Lys Leu Ser Lys Arg Gln Gly Leu Ala Ser Thr
        1090                1095                1100
Arg Val Ala Met Glu Ser Asn Ala Gly Ala Phe Ile Glu Arg Thr Leu
1105                1110                1115                1120
```

```
Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
                1140                1145                1150

Gln His Leu Ile Asp Glu Val Gln Ala Val Tyr Arg Ala Gln Gly Val
                1155                1160                1165

Ala Ile His Asp Lys His Ile Glu Ile Ile Arg Gln Met Leu Arg
        1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
                1205                1210                1215

Ala Gly Gly Gln Pro Ala Glu Leu Arg Ser Glu Ile Met Gly Ile Thr
                1220                1225                1230

Lys Ala Ser Leu Ala Thr Glu Ser Trp Leu Ser Ala Ala Ser Phe Gln
                1235                1240                1245

Glu Thr Thr Arg Val Leu Thr Asp Ala Ala Ile Asn Lys Arg Ser Asp
                1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
                1285                1290                1295

Glu Ala Ala Arg Asn Ala Ala Tyr Ser Ile Pro Thr Tyr Gly Glu Ser
                1300                1305                1310

Ile Tyr Gly Asp Asp Gly Phe Gly Glu Phe Thr Gly Ala Ser Val Pro
                1315                1320                1325

Leu Asp Glu Ala Phe
    1330

<210> SEQ ID NO 9
<211> LENGTH: 1333
<212> TYPE: PRT
<213> ORGANISM: Artificial Sequence
<220> FEATURE:
<223> OTHER INFORMATION: RpoC of KCCM11016P-rpoC(M2)

<400> SEQUENCE: 9

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140
```

-continued

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
        435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
    530                 535                 540

Leu Pro Leu Ser Ala Glu Ala Gln Ala Glu Ala Arg Val Leu Met Leu
545                 550                 555                 560

-continued

```
Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
    610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
        675                 680                 685

Gly Val Met Val Arg Lys Gly Gly Ser Asp Lys Ile Met Leu Gly
    690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
        755                 760                 765

Lys Tyr Asn Arg Gly Lys Leu Thr Gly Arg Glu Arg Tyr Asp Arg Leu
    770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
        835                 840                 845

Ser Phe Arg Glu Gly Leu Thr Val Leu Glu Tyr Phe Asn Asn Ser His
    850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
    930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
```

```
                980             985             990
Cys Tyr Gly Lys Ser Met Ala Ser Gly Gln Gln Val Asp Ile Gly Glu
            995                1000                1005

Ala Val Gly Ile Val Ala Ala Gln Ser Ile Gly Glu Pro Gly Thr Gln
       1010                1015                1020

Leu His Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
       1060                1065                1070

Glu Gly Asn Phe Tyr Thr Leu Thr Ile Val Pro Asp Asp Gly Ser Asp
            1075                1080                1085

Asn Val Val Tyr Glu Lys Leu Ser Lys Arg Gln Gly Leu Ala Ser Thr
       1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
            1125                1130                1135

Ala Asp Pro His Asp Val Leu Glu Ile Leu Gly Arg Arg Gly Val Glu
       1140                1145                1150

Gln His Leu Ile Asp Glu Val Gln Ala Val Tyr Arg Ala Gln Gly Val
       1155                1160                1165

Ala Ile His Asp Lys His Ile Glu Ile Ile Arg Gln Met Leu Arg
       1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
            1220                1225                1230

Lys Ala Ser Leu Ala Thr Glu Ser Trp Leu Ser Ala Ala Ser Phe Gln
       1235                1240                1245

Glu Thr Thr Arg Val Leu Thr Asp Ala Ala Ile Asn Lys Arg Ser Asp
1250                1255                1260

Lys Leu Ile Gly Leu Lys Glu Asn Val Ile Ile Gly Lys Leu Ile Pro
       1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
       1300                1305                1310

Ile Tyr Gly Asp Asp Gly Phe Gly Glu Phe Thr Gly Ala Ser Val Pro
       1315                1320                1325

Leu Asp Glu Ala Phe
   1330

<210> SEQ ID NO 10
<211> LENGTH: 1333
<212> TYPE: PRT
<213> ORGANISM: Artificial Sequence
<220> FEATURE:
<223> OTHER INFORMATION: RpoC of KCCM11016P-rpoC(M3)

<400> SEQUENCE: 10

Met Leu Asp Val Asn Val Phe Asp Glu Leu Arg Ile Gly Leu Ala Thr
```

```
  1               5                    10                   15
Ala Asp Asp Ile Arg Arg Trp Ser Lys Gly Glu Val Lys Lys Pro Glu
                20                  25                  30

Thr Ile Asn Tyr Arg Thr Leu Lys Pro Glu Lys Asp Gly Leu Phe Cys
                35                  40                  45

Glu Arg Ile Phe Gly Pro Thr Arg Asp Trp Glu Cys Ala Cys Gly Lys
                50                  55                  60

Tyr Lys Arg Val Arg Tyr Lys Gly Ile Ile Cys Glu Arg Cys Gly Val
 65                 70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
               100                 105                 110

Arg Leu Gly Tyr Leu Leu Asp Leu Ala Pro Lys Asp Leu Asp Leu Ile
               115                 120                 125

Ile Tyr Phe Gly Ala Asn Ile Ile Thr Ser Val Asp Glu Glu Ala Arg
               130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
                180                 185                 190

Ala Arg Arg Lys Val Gln Ala Ala Asp Lys Glu Met Gln His Ile
                195                 200                 205

Arg Glu Arg Ala Gln Arg Glu Ile Asp Arg Leu Asp Glu Val Trp Gln
                210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
                260                 265                 270

Glu Ala Glu Glu Leu Arg Asp Ile Ile Asn Asn Gly Lys Gly Gln Lys
                275                 280                 285

Lys Met Arg Ala Leu Lys Arg Leu Lys Val Val Ala Ala Phe Gln Arg
290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
                340                 345                 350

Arg Leu Lys Arg Met Ile Glu Leu Gly Ala Pro Glu Ile Ile Val Asn
                355                 360                 365

Asn Glu Lys Arg Met Leu Gln Glu Ser Val Asp Ala Leu Phe Asp Asn
                370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
                420                 425                 430
```

-continued

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
    530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
    595                 600                 605

Asn Gly Pro Glu Lys Gly Val Tyr Ser Ser Leu Ala Glu Ala Ile Met
            610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
    675                 680                 685

Gly Val Met Val Arg Lys Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
    755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
    835                 840                 845

```
Ser Phe Arg Glu Gly Leu Thr Val Leu Glu Tyr Phe Asn Asn Ser His
850                     855                     860

Gly Ser Arg Lys Gly Leu Ala Asp Thr Ala Leu Arg Thr Ala Asp Ser
865                     870                     875                 880

Gly Tyr Leu Thr Arg Arg Leu Val Asp Val Ala Gln Asp Val Ile Val
                885                     890                     895

Arg Val Glu Asp Cys Gly Thr Arg Gln Gly Val Arg Val Pro Val Ala
            900                     905                     910

Ala Glu Val Leu Asp Ala Thr Gly Ala Val Thr Gly Tyr Thr Arg His
            915                     920                     925

Asp Leu Ile Glu Thr Ser Val Ser Gly Arg Val Leu Ala Gly Asp Ala
930                     935                     940

Thr Asn Ala Ala Gly Glu Val Val Leu Ala Ala Gly Thr Asp Leu Thr
945                     950                     955                 960

Glu Leu Asn Ile Asp Leu Leu Val Glu Ala Gly Ile Lys Asp Val Lys
                965                     970                     975

Val Arg Ser Val Leu Thr Cys Gln Thr Pro Thr Gly Val Cys Ala Lys
            980                     985                     990

Cys Tyr Gly Lys Ser Met Ala Ser Gly Gln Gln Val Asp Ile Gly Glu
            995                     1000                    1005

Ala Val Gly Ile Val Ala Ala Gln Ser Ile Gly Glu Pro Gly Thr Gln
            1010                    1015                    1020

Leu Thr Met Arg Thr Phe His Gln Gly Gly Val Gly Gly Asp Ile Thr
1025                    1030                    1035                1040

Gly Gly Leu Pro Arg Val Gln Glu Leu Phe Glu Ala Arg Val Pro Lys
            1045                    1050                    1055

Asn Cys Ala Pro Ile Ala Ser Val Glu Gly Val Ile His Leu Glu Asp
            1060                    1065                    1070

Glu Gly Asn Phe Tyr Thr Leu Thr Ile Val Pro Asp Asp Gly Ser Asp
            1075                    1080                    1085

Asn Val Val Tyr Glu Lys Leu Ser Lys Arg Gln Gly Leu Ala Ser Thr
            1090                    1095                    1100

Arg Val Ala Met Glu Ser Asn Ala Gly Ala Phe Ile Glu Arg Thr Leu
1105                    1110                    1115                1120

Thr Glu Gly Asp Arg Val Thr Val Gly Gln Arg Leu Leu Arg Gly Ala
            1125                    1130                    1135

Ala Asp Pro His Asp Val Leu Glu Ile Leu Gly Arg Arg Gly Val Glu
            1140                    1145                    1150

Gln His Leu Ile Asp Glu Val Gln Ala Val Tyr Arg Ala Gln Gly Val
            1155                    1160                    1165

Ala Ile His Asp Lys His Ile Glu Ile Ile Arg Gln Met Leu Arg
1170                    1175                    1180

Arg Gly Thr Val Ile Glu Ser Gly Ser Thr Glu Phe Leu Pro Gly Ser
1185                    1190                    1195                1200

Leu Val Asp Leu Ser Glu Ala Lys Leu Ala Asn Ser Glu Ala Ile Gly
            1205                    1210                    1215

Ala Gly Gly Gln Pro Ala Glu Leu Arg Ser Glu Ile Met Gly Ile Thr
            1220                    1225                    1230

Lys Ala Ser Leu Ala Thr Glu Ser Trp Leu Ser Ala Ala Ser Lys Gln
            1235                    1240                    1245

Glu Thr Thr Arg Val Leu Thr Asp Ala Ala Ile Asn Lys Arg Ser Asp
            1250                    1255                    1260

Lys Leu Ile Gly Leu Lys Glu Asn Val Ile Ile Gly Lys Leu Ile Pro
```

```
1265                1270                1275                1280
Ala Gly Thr Gly Ile Ser Arg Tyr Arg Asn Ile Ser Ile Lys Pro Thr
                1285                1290                1295
Glu Ala Ala Arg Asn Ala Ala Tyr Ser Ile Pro Thr Tyr Gly Glu Ser
        1300                1305                1310
Ile Tyr Gly Asp Asp Gly Phe Gly Glu Phe Thr Gly Ala Ser Val Pro
        1315                1320                1325
Leu Asp Glu Ala Phe
    1330

<210> SEQ ID NO 11
<211> LENGTH: 1333
<212> TYPE: PRT
<213> ORGANISM: Artificial Sequence
<220> FEATURE:
<223> OTHER INFORMATION: RpoC of KCCM11016P-rpoC(M4)

<400> SEQUENCE: 11

Met Leu Asp Val Asn Val Phe Asp Glu Leu Arg Ile Gly Leu Ala Thr
 1               5                  10                  15

Ala Asp Asp Ile Arg Arg Gly Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
```

-continued

```
            290                 295                 300
Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Arg Phe Ala
                325                 330                 335

Thr Ser Asp Leu Asn Asp Leu Tyr Arg Arg Val Ile Asn Arg Asn Asn
                340                 345                 350

Arg Leu Lys Arg Met Ile Glu Leu Gly Ala Pro Glu Ile Ile Val Asn
                355                 360                 365

Asn Glu Lys Arg Met Leu Gln Glu Ser Val Asp Ala Leu Phe Asp Asn
                370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
                420                 425                 430

Gly Pro Gln Leu Arg Leu His Glu Cys Gly Leu Pro Lys Leu Met Ala
                435                 440                 445

Leu Glu Leu Phe Lys Pro Phe Val Met Lys Arg Leu Val Glu Asn Glu
                450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
                500                 505                 510

Glu Pro Val Leu Val Glu Gly Lys Ala Ile Gln Leu His Pro Leu Ala
                515                 520                 525

Cys Glu Ala Phe Asn Ala Asp Phe Asp Gly Asp Gln Met Ala Val His
                530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
                580                 585                 590

Ser Ser Glu Glu Phe Gly Gly Gln Gly Ala Tyr Gln Pro Ala Asp Glu
                595                 600                 605

Asn Gly Pro Glu Lys Gly Val Tyr Ser Ser Leu Ala Glu Ala Ile Met
                610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
                660                 665                 670

Arg Val Met Phe Asn Glu Ile Leu Pro Trp Asn Tyr Pro Tyr Leu Glu
                675                 680                 685

Gly Val Met Val Arg Lys Gly Gly Ser Asp Lys Ile Met Leu Gly
                690                 695                 700

Asp Val Val Asn Asp Leu Ala Ala Lys Tyr Pro Met Ile Thr Val Ala
705                 710                 715                 720
```

-continued

```
Gln Thr Met Asp Lys Met Lys Asp Ala Gly Phe Tyr Trp Ser Thr Arg
            725                 730                 735
Ser Gly Val Thr Ile Ala Met Ser Asp Val Leu Val Leu Pro Asn Lys
        740                 745                 750
Glu Glu Met Leu Asp Arg Tyr Glu Glu Ser Ala Arg Gln Ile Glu Val
    755                 760                 765
Lys Tyr Asn Arg Gly Lys Leu Thr Gly Arg Glu Arg Tyr Asp Arg Leu
770                 775                 780
Val Glu Leu Trp Lys Asp Ala Thr Asp Glu Val Gly Gln Ala Val Glu
785                 790                 795                 800
Asp Leu Tyr Pro Asp Asn Pro Ile Pro Met Ile Val Lys Ser Gly
            805                 810                 815
Ala Ala Gly Asn Met Arg Gln Ile Trp Thr Leu Ala Gly Met Lys Gly
        820                 825                 830
Met Val Val Asn Ser Lys Gly Asp Tyr Ile Thr Arg Pro Ile Lys Thr
    835                 840                 845
Ser Phe Arg Glu Gly Leu Thr Val Leu Glu Tyr Phe Asn Asn Ser His
850                 855                 860
Gly Ser Arg Lys Gly Leu Ala Asp Thr Ala Leu Arg Thr Ala Asp Ser
865                 870                 875                 880
Gly Tyr Leu Thr Arg Arg Leu Val Asp Val Ala Gln Asp Val Ile Val
            885                 890                 895
Arg Val Glu Asp Cys Gly Thr Arg Gln Gly Val Arg Val Pro Val Ala
        900                 905                 910
Ala Glu Val Leu Asp Ala Thr Gly Ala Val Thr Gly Tyr Thr Arg His
    915                 920                 925
Asp Leu Ile Glu Thr Ser Val Ser Gly Arg Val Leu Ala Gly Asp Ala
930                 935                 940
Thr Asn Ala Ala Gly Glu Val Val Leu Ala Ala Gly Thr Asp Leu Thr
945                 950                 955                 960
Glu Leu Asn Ile Asp Leu Leu Val Glu Ala Gly Ile Lys Asp Val Lys
            965                 970                 975
Val Arg Ser Val Leu Thr Cys Gln Thr Pro Thr Gly Val Cys Ala Lys
        980                 985                 990
Cys Tyr Glu Lys Ser Met Ala Ser Gly Gln Gln Val Asp Ile Gly Glu
    995                 1000                1005
Ala Val Gly Ile Val Ala Ala Gln Ser Cys Gly Glu Pro Gly Thr Gln
1010                1015                1020
Leu Thr Met Arg Thr Phe His Gln Gly Gly Val Gly Gly Asp Ile Thr
1025                1030                1035                1040
Gly Gly Leu Pro Arg Val Gln Glu Leu Phe Glu Ala Arg Val Pro Lys
            1045                1050                1055
Asn Cys Ala Pro Ile Ala Ser Val Glu Gly Val Ile His Leu Glu Asp
        1060                1065                1070
Glu Gly Asn Phe Tyr Thr Leu Thr Ile Val Pro Asp Asp Gly Ser Asp
    1075                1080                1085
Asn Val Val Tyr Glu Lys Leu Ser Lys Arg Gln Gly Leu Ala Ser Thr
1090                1095                1100
Arg Val Ala Met Glu Ser Asn Ala Gly Ala Phe Ile Glu Arg Thr Leu
1105                1110                1115                1120
Thr Glu Gly Asp Arg Val Thr Val Gly Gln Arg Leu Leu Arg Gly Ala
            1125                1130                1135
```

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
        1155                1160                1165

Ala Ile His Asp Lys His Ile Glu Ile Ile Arg Gln Met Leu Arg
        1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
                1205                1210                1215

Ala Gly Gly Gln Pro Ala Glu Leu Arg Ser Glu Ile Met Gly Ile Thr
        1220                1225                1230

Lys Ala Ser Leu Ala Thr Glu Ser Trp Leu Ser Ala Ala Ser Phe Gln
        1235                1240                1245

Glu Thr Thr Arg Val Leu Thr Asp Ala Ala Ile Asn Lys Arg Ser Asp
        1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
        1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
        1315                1320                1325

Leu Asp Glu Ala Phe
    1330

<210> SEQ ID NO 12
<211> LENGTH: 1333
<212> TYPE: PRT
<213> ORGANISM: Artificial Sequence
<220> FEATURE:
<223> OTHER INFORMATION: RpoC of KCCM11016P-rpoC(M5)

<400> SEQUENCE: 12

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

```
Asp Val Glu Ala Asp Ala Glu Ser Asp Ile Ala Glu Arg Ala Glu Lys
            165                 170                 175
Leu Glu Glu Asp Leu Ala Glu Leu Glu Ala Ala Gly Ala Lys Ala Asp
        180                 185                 190
Ala Arg Arg Lys Val Gln Ala Ala Asp Lys Glu Met Gln His Ile
    195                 200                 205
Arg Glu Arg Ala Gln Arg Glu Ile Asp Arg Leu Asp Glu Val Trp Gln
    210                 215                 220
Thr Phe Ile Lys Leu Ala Pro Lys Gln Met Ile Arg Asp Glu Lys Leu
225                 230                 235                 240
Tyr Asp Glu Leu Ile Asp Arg Tyr Glu Asp Tyr Phe Thr Gly Gly Met
                245                 250                 255
Gly Ala Glu Ser Ile Glu Ala Leu Ile Gln Asn Phe Asp Leu Asp Ala
            260                 265                 270
Glu Ala Glu Glu Leu Arg Asp Ile Ile Asn Asn Gly Lys Gly Gln Lys
        275                 280                 285
Lys Met Arg Ala Leu Lys Arg Leu Lys Val Val Ala Ala Phe Gln Arg
    290                 295                 300
Ser Gly Asn Asp Pro Ala Gly Met Val Leu Asn Ala Ile Pro Val Ile
305                 310                 315                 320
Pro Pro Glu Leu Arg Pro Met Val Gln Leu Asp Gly Gly Arg Phe Ala
                325                 330                 335
Thr Ser Asp Leu Asn Asp Leu Tyr Arg Arg Val Ile Asn Arg Asn Asn
            340                 345                 350
Arg Leu Lys Arg Met Ile Glu Leu Gly Ala Pro Glu Ile Ile Val Asn
        355                 360                 365
Asn Glu Lys Arg Met Leu Gln Glu Ser Val Asp Ala Leu Phe Asp Asn
    370                 375                 380
Gly Arg Arg Gly Arg Pro Val Thr Gly Pro Gly Asn Arg Pro Leu Lys
385                 390                 395                 400
Ser Leu Ser Asp Leu Leu Lys Gly Lys Gln Gly Arg Phe Arg Gln Asn
                405                 410                 415
Leu Leu Gly Lys Arg Val Asp Tyr Ser Gly Arg Ser Val Ile Ile Val
            420                 425                 430
Gly Pro Gln Leu Arg Leu His Glu Cys Gly Leu Pro Lys Leu Met Ala
        435                 440                 445
Leu Glu Leu Phe Lys Pro Phe Val Met Lys Arg Leu Val Glu Asn Glu
    450                 455                 460
Tyr Ala Gln Asn Ile Lys Ser Ala Lys Arg Met Val Glu Arg Gln Arg
465                 470                 475                 480
Pro Glu Val Trp Asp Val Leu Glu Glu Ala Ile Ser Glu His Pro Val
                485                 490                 495
Met Leu Asn Arg Ala Pro Thr Leu His Arg Leu Gly Ile Gln Ala Phe
            500                 505                 510
Glu Pro Val Leu Val Glu Gly Lys Ala Ile Gln Leu His Pro Leu Ala
        515                 520                 525
Cys Glu Ala Phe Asn Ala Asp Phe Asp Gly Asp Gln Met Ala Val His
    530                 535                 540
Leu Pro Leu Ser Ala Glu Ala Gln Ala Glu Ala Arg Val Leu Met Leu
545                 550                 555                 560
Ala Ser Asn Asn Ile Leu Ser Pro Ala Ser Gly Lys Pro Leu Ala Met
                565                 570                 575
Pro Arg Leu Asp Met Val Thr Gly Leu Tyr Tyr Leu Thr Leu Glu Lys
```

```
              580             585             590
Ser Ser Glu Glu Phe Gly Gly Gln Gly Ala Tyr Gln Pro Ala Asp Glu
        595                 600             605

Asn Gly Pro Glu Lys Gly Val Tyr Ser Ser Leu Ala Glu Ala Ile Met
610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
                660                 665                 670

Arg Val Met Phe Asn Glu Ile Leu Pro Trp Asn Tyr Pro Tyr Leu Glu
            675                 680                 685

Gly Val Met Val Arg Lys Gly Gly Ser Asp Lys Ile Met Leu Gly
690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
                820                 825                 830

Met Val Val Asn Ser Lys Gly Asp Tyr Ile Thr Arg Pro Ile Lys Thr
            835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
            915                 920                 925

Asp Leu Ile Glu Thr Ser Val Ser Gly Arg Val Leu Ala Gly Asp Ala
930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr His Lys Ser Met Ala Ser Gly Gln Gln Val Asp Ile Gly Glu
            995                 1000                1005
```

-continued

Ala Val Gly Ile Val Ala Ala Gln Ser Cys Gly Glu Pro Gly Thr Gln
            1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
                1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
        1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
        1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Cys Thr
        1220                1225                1230

Lys Ala Ser Leu Ala Thr Glu Ser Trp Leu Ser Ala Ala Ser Phe Gln
    1235                1240                1245

Glu Thr Thr Arg Val Leu Thr Asp Ala Ala Ile Asn Lys Arg Ser Asp
1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
    1315                1320                1325

Leu Asp Glu Ala Phe
    1330

<210> SEQ ID NO 13
<211> LENGTH: 1334
<212> TYPE: PRT
<213> ORGANISM: Artificial Sequence
<220> FEATURE:
<223> OTHER INFORMATION: RpoC of KCCM11016P-rpoC(M6)

<400> SEQUENCE: 13

Met Leu Asp Val Asn Val Phe Asp Glu Leu Arg Ile Gly Leu Ala Thr
 1               5                  10                  15

Ala Asp Asp Ile Arg Arg Trp Ser Lys Gly Glu Val Lys Lys Pro Glu
            20                  25                  30

```
Thr Ile Asn Tyr Arg Thr Leu Lys Pro Glu Lys Asp Gly Leu Phe Cys
         35                  40                  45
Glu Arg Ile Phe Gly Pro Thr Arg Asp Trp Glu Cys Ala Cys Gly Lys
 50                  55                  60
Tyr Lys Arg Val Arg Tyr Lys Gly Ile Ile Cys Glu Arg Cys Gly Val
 65                  70                  75                  80
Glu Val Thr Lys Ser Lys Val Arg Arg Glu Arg Met Gly His Ile Glu
                 85                  90                  95
Leu Ala Ala Pro Val Thr His Ile Trp Tyr Phe Lys Gly Val Pro Ser
                100                 105                 110
Arg Leu Gly Tyr Leu Leu Asp Leu Ala Pro Lys Asp Leu Asp Leu Ile
                115                 120                 125
Ile Tyr Phe Gly Ala Asn Ile Ile Thr Ser Val Asp Glu Glu Ala Arg
                130                 135                 140
His Ser Asp Gln Thr Thr Leu Glu Ala Glu Met Leu Leu Glu Lys Lys
145                 150                 155                 160
Asp Val Glu Ala Asp Ala Glu Ser Asp Ile Ala Glu Arg Ala Glu Lys
                165                 170                 175
Leu Glu Glu Asp Leu Ala Glu Leu Glu Ala Ala Gly Ala Lys Ala Asp
                180                 185                 190
Ala Arg Arg Lys Val Gln Ala Ala Asp Lys Glu Met Gln His Ile
                195                 200                 205
Arg Glu Arg Ala Gln Arg Glu Ile Asp Arg Leu Asp Glu Val Trp Gln
                210                 215                 220
Thr Phe Ile Lys Leu Ala Pro Lys Gln Met Ile Arg Asp Glu Lys Leu
225                 230                 235                 240
Tyr Asp Glu Leu Ile Asp Arg Tyr Glu Asp Tyr Phe Thr Gly Gly Met
                245                 250                 255
Gly Ala Glu Ser Ile Glu Ala Leu Ile Gln Asn Phe Asp Leu Asp Ala
                260                 265                 270
Glu Ala Glu Glu Leu Arg Asp Ile Ile Asn Asn Gly Lys Gly Gln Lys
                275                 280                 285
Lys Met Arg Ala Leu Lys Arg Leu Lys Val Val Ala Ala Phe Gln Arg
290                 295                 300
Ser Gly Asn Asp Pro Ala Gly Met Val Leu Asn Ala Ile Pro Val Ile
305                 310                 315                 320
Pro Pro Glu Leu Arg Pro Met Val Gln Leu Asp Gly Gly Arg Phe Ala
                325                 330                 335
Thr Ser Asp Leu Asn Asp Leu Tyr Arg Arg Val Ile Asn Arg Asn Asn
                340                 345                 350
Arg Leu Lys Arg Met Ile Glu Leu Gly Ala Pro Glu Ile Ile Val Asn
                355                 360                 365
Asn Glu Lys Arg Met Leu Gln Glu Ser Val Asp Ala Leu Phe Asp Asn
                370                 375                 380
Gly Arg Arg Gly Arg Pro Val Thr Gly Pro Gly Asn Arg Pro Leu Lys
385                 390                 395                 400
Ser Leu Ser Asp Leu Leu Lys Gly Lys Gln Gly Arg Phe Arg Gln Asn
                405                 410                 415
Leu Leu Gly Lys Arg Val Asp Tyr Ser Gly Arg Ser Val Ile Ile Val
                420                 425                 430
Gly Pro Gln Leu Arg Leu His Glu Cys Gly Leu Pro Lys Leu Met Ala
                435                 440                 445
```

```
Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
            610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685

Gly Val Met Val Arg Lys Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
            835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
```

```
                865                 870                 875                 880
        Gly Tyr Leu Thr Arg Arg Leu Val Asp Val Ala Gln Asp Val Ile Val
                            885                 890                 895
        Arg Val Glu Asp Cys Gly Thr Arg Gln Gly Val Arg Val Pro Val Ala
                        900                 905                 910
        Ala Glu Val Leu Asp Ala Thr Gly Ala Val Thr Gly Tyr Thr Arg His
                        915                 920                 925
        Asp Leu Ile Glu Thr Ser Val Ser Gly Arg Val Leu Ala Gly Asp Ala
                    930                 935                 940
        Thr Asn Ala Ala Gly Glu Val Val Leu Ala Ala Gly Thr Asp Leu Thr
        945                 950                 955                 960
        Glu Leu Asn Ile Asp Leu Leu Val Glu Ala Gly Ile Lys Asp Val Lys
                            965                 970                 975
        Val Arg Ser Val Leu Thr Cys Gln Thr Pro Thr Gly Val Cys Ala Lys
                        980                 985                 990
        Cys Tyr Gly Lys Ser Met Ala Ser Gly Gln Gln Val Asp Ile Gly Glu
                        995                 1000                1005
        Ala Val Gly Ile Val Ala Ala Gln Ser Ile Gly Glu Pro Gly Thr Gln
                    1010                1015                1020
        Leu Thr Met Arg Thr Phe His Gln Gly Gly Val Gly Gly Asp Ile Thr
        1025                1030                1035                1040
        Gly Gly Leu Pro Arg Val Gln Glu Leu Phe Glu Ala Arg Val Pro Lys
                            1045                1050                1055
        Asn Cys Ala Pro Ile Ala Ser Val Glu Gly Val Ile His Leu Glu Asp
                        1060                1065                1070
        Glu Gly Asn Phe Tyr Thr Leu Thr Ile Val Pro Asp Asp Gly Ser Asp
                        1075                1080                1085
        Asn Val Val Tyr Glu Lys Leu Ser Lys Arg Gln Gly Leu Ala Ser Thr
                    1090                1095                1100
        Arg Val Ala Met Glu Ser Asn Ala Gly Ala Phe Ile Glu Arg Thr Leu
        1105                1110                1115                1120
        Thr Glu Gly Asp Arg Val Thr Val Gly Gln Arg Leu Leu Arg Gly Ala
                            1125                1130                1135
        Ala Asp Pro His Asp Val Leu Glu Ile Leu Gly Arg Arg Gly Val Glu
                        1140                1145                1150
        Gln His Leu Ile Asp Glu Val Gln Ala Val Tyr Arg Ala Gln Gly Val
                        1155                1160                1165
        Ala Ile His Asp Lys His Ile Glu Ile Ile Arg Gln Met Leu Arg
                    1170                1175                1180
        Arg Gly Thr Val Ile Glu Ser Gly Ser Thr Glu Phe Leu Pro Gly Ser
        1185                1190                1195                1200
        Leu Val Asp Leu Ser Glu Ala Lys Leu Ala Asn Ser Glu Ala Ile Gly
                            1205                1210                1215
        Ala Gly Gly Gln Pro Ala Glu Leu Arg Ser Glu Ile Met Gly Ile Thr
                        1220                1225                1230
        Lys Ala Ser Leu Ala Thr Glu Ser Trp Leu Ser Ala Ala Ser Phe Gln
                        1235                1240                1245
        Glu Thr Thr Thr Thr Val Leu Thr Asp Ala Ala Ile Asn Lys Arg Ser
                    1250                1255                1260
        Asp Lys Leu Ile Gly Leu Lys Glu Asn Val Ile Ile Gly Lys Leu Ile
        1265                1270                1275                1280
        Pro Ala Gly Thr Gly Ile Ser Arg Tyr Arg Asn Ile Ser Ile Lys Pro
                            1285                1290                1295
```

-continued

```
Thr Glu Ala Ala Arg Asn Ala Ala Tyr Ser Ile Pro Thr Tyr Gly Glu
            1300                1305                1310

Ser Ile Tyr Gly Asp Asp Gly Phe Gly Glu Phe Thr Gly Ala Ser Val
        1315                1320                1325

Pro Leu Asp Glu Ala Phe
    1330

<210> SEQ ID NO 14
<211> LENGTH: 1333
<212> TYPE: PRT
<213> ORGANISM: Artificial Sequence
<220> FEATURE:
<223> OTHER INFORMATION: RpoC of KCCM11016P-rpoC(M7)

<400> SEQUENCE: 14

Met Leu Asp Val Asn Val Phe Asp Glu Leu Arg Ile Gly Leu Ala Thr
 1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
    290                 295                 300

Ser Gly Asn Asp Pro Ala Gly Met Val Leu Asn Ala Ile Pro Val Ile
305                 310                 315                 320
```

```
Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
    370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
        435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
    530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
    610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
        675                 680                 685

Gly Val Met Val Arg Lys Gly Gly Ser Asp Lys Ile Met Leu Gly
    690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735
```

-continued

```
Ser Gly Val Thr Ile Ala Met Ser Asp Val Leu Val Leu Pro Asn Lys
            740                 745                 750

Glu Glu Met Leu Asp Arg Tyr Glu Gly Ser Ala Arg Gln Ile Glu Val
        755                 760                 765

Lys Tyr Asn Arg Gly Lys Leu Thr Gly Arg Glu Arg Tyr Asp Arg Leu
    770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
        835                 840                 845

Ser Phe Arg Glu Gly Leu Thr Val Leu Glu Tyr Phe Asn Asn Ser His
    850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
    930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
        995                 1000                1005

Ala Val Gly Ile Val Ala Ala Gln Ser Ile Gly Glu Pro Arg Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
                1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
        1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
```

```
                    1155                1160                1165

Ala Ile His Asp Lys His Ile Glu Ile Ile Arg Gln Met Leu Arg
        1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
            1220                1225                1230

Lys Ala Ser Leu Ala Thr Glu Ser Trp Leu Ser Ala Ala Ser Phe Gln
            1235                1240                1245

Glu Thr Thr Arg Val Leu Thr Asp Ala Ala Ile Asn Lys Arg Ser Asp
        1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
            1300                1305                1310

Ile Tyr Gly Asp Asp Gly Phe Gly Glu Phe Thr Gly Ala Ser Val Pro
        1315                1320                1325

Leu Asp Glu Ala Phe
        1330

<210> SEQ ID NO 15
<211> LENGTH: 1333
<212> TYPE: PRT
<213> ORGANISM: Artificial Sequence
<220> FEATURE:
<223> OTHER INFORMATION: RpoC of KCCM11016P-rpoC(M8)

<400> SEQUENCE: 15

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
```

-continued

```
                180                 185                 190
Ala Arg Arg Lys Val Gln Ala Ala Asp Lys Glu Met Gln His Ile
            195                 200                 205
Arg Glu Arg Ala Gln Arg Glu Ile Asp Arg Leu Asp Glu Val Trp Gln
            210                 215                 220
Thr Phe Ile Lys Leu Ala Pro Lys Gln Met Ile Arg Asp Glu Lys Leu
225                 230                 235                 240
Tyr Asp Glu Leu Ile Asp Arg Tyr Glu Asp Tyr Phe Thr Gly Gly Met
                245                 250                 255
Gly Ala Glu Ser Ile Glu Ala Leu Ile Gln Asn Phe Asp Leu Asp Ala
            260                 265                 270
Glu Ala Glu Glu Leu Arg Asp Ile Ile Asn Asn Gly Lys Gly Gln Lys
            275                 280                 285
Lys Met Arg Ala Leu Lys Arg Leu Lys Val Val Ala Ala Phe Gln Arg
        290                 295                 300
Ser Gly Asn Asp Pro Ala Gly Met Val Leu Asn Ala Ile Pro Val Ile
305                 310                 315                 320
Pro Pro Glu Leu Arg Pro Met Val Gln Leu Asp Gly Gly Arg Phe Ala
                325                 330                 335
Thr Ser Asp Leu Asn Asp Leu Tyr Arg Arg Val Ile Asn Arg Asn Asn
                340                 345                 350
Arg Leu Lys Arg Met Ile Glu Leu Gly Ala Pro Glu Ile Ile Val Asn
            355                 360                 365
Asn Glu Lys Arg Met Leu Gln Glu Ser Val Asp Ala Leu Phe Asp Asn
        370                 375                 380
Gly Arg Arg Gly Arg Pro Val Thr Gly Pro Gly Asn Arg Pro Leu Lys
385                 390                 395                 400
Ser Leu Ser Asp Leu Leu Lys Gly Lys Gln Gly Arg Phe Arg Gln Asn
                405                 410                 415
Leu Leu Gly Lys Arg Val Asp Tyr Ser Gly Arg Ser Val Ile Ile Val
            420                 425                 430
Gly Pro Gln Leu Arg Leu His Glu Cys Gly Leu Pro Lys Leu Met Ala
        435                 440                 445
Leu Glu Leu Phe Lys Pro Phe Val Met Lys Arg Leu Val Glu Asn Glu
    450                 455                 460
Tyr Ala Gln Asn Ile Lys Ser Ala Lys Arg Met Val Glu Arg Gln Arg
465                 470                 475                 480
Pro Glu Val Trp Asp Val Leu Glu Glu Ala Ile Ser Glu His Pro Val
                485                 490                 495
Met Leu Asn Arg Ala Pro Thr Leu His Arg Leu Gly Ile Gln Ala Phe
            500                 505                 510
Glu Pro Val Leu Val Glu Gly Lys Ala Ile Gln Leu His Pro Leu Ala
            515                 520                 525
Cys Glu Ala Phe Asn Ala Asp Phe Asp Gly Asp Gln Met Ala Val His
        530                 535                 540
Leu Pro Leu Ser Ala Glu Ala Gln Ala Glu Ala Arg Val Leu Met Leu
545                 550                 555                 560
Ala Ser Asn Asn Ile Leu Ser Pro Ala Ser Gly Lys Pro Leu Ala Met
                565                 570                 575
Pro Arg Leu Asp Met Val Thr Gly Leu Tyr Tyr Leu Thr Leu Glu Lys
            580                 585                 590
Ser Ser Glu Glu Phe Gly Gly Gln Gly Ala Tyr Gln Pro Ala Asp Glu
        595                 600                 605
```

-continued

Asn Gly Pro Glu Lys Gly Val Tyr Ser Ser Leu Ala Glu Ala Ile Met
610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
        675                 680                 685

Gly Val Met Val Arg Lys Gly Gly Ser Asp Lys Ile Met Leu Gly
690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
        755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
        835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
        995                 1000                1005

Ala Val Gly Ile Val Ala Asp Gln Ser Ile Gly Glu Pro Gly Thr Gln
    1010                1015                1020

```
Leu Thr Met Arg Thr Phe His Gln Gly Gly Val Gly Gly Asp Ile Thr
         1025                1030                1035                1040

Gly Gly Leu Pro Arg Val Gln Glu Leu Phe Glu Ala Arg Val Pro Lys
         1045                1050                1055

Asn Cys Ala Pro Ile Ala Ser Val Glu Gly Val Ile His Leu Glu Asp
         1060                1065                1070

Glu Gly Asn Phe Tyr Thr Leu Thr Ile Val Pro Asp Asp Gly Ser Asp
         1075                1080                1085

Asn Val Val Tyr Glu Lys Leu Ser Lys Arg Gln Gly Leu Ala Ser Thr
         1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
         1125                1130                1135

Ala Asp Pro His Asp Val Leu Glu Ile Leu Gly Arg Arg Gly Val Glu
         1140                1145                1150

Gln His Leu Ile Asp Glu Val Gln Ala Val Tyr Arg Ala Gln Gly Val
         1155                1160                1165

Ala Ile His Asp Lys His Ile Glu Ile Ile Arg Gln Met Leu Arg
         1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
         1205                1210                1215

Ala Gly Gly Gln Pro Ala Glu Leu Arg Ser Glu Ile Met Gly Ile Thr
         1220                1225                1230

Lys Ala Ser Leu Ala Thr Glu Ser Trp Leu Ser Ala Ala Ser Phe Gln
         1235                1240                1245

Glu Thr Thr Arg Val Leu Thr Asp Ala Ala Ile Asn Lys Arg Ser Asp
         1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
         1285                1290                1295

Glu Ala Ala Arg Asn Ala Ala Tyr Ser Ile Pro Thr Tyr Gly Glu Ser
         1300                1305                1310

Ile Tyr Gly Asp Asp Gly Phe Gly Glu Phe Thr Gly Ala Ser Val Pro
         1315                1320                1325

Leu Asp Glu Ala Phe
         1330

<210> SEQ ID NO 16
<211> LENGTH: 1333
<212> TYPE: PRT
<213> ORGANISM: Artificial Sequence
<220> FEATURE:
<223> OTHER INFORMATION: RpoC of KCCM11016P-rpoC(M9)

<400> SEQUENCE: 16

Met Leu Asp Val Asn Val Phe Asp Glu Leu Arg Ile Gly Leu Ala Thr
 1               5                  10                  15

Ala Asp Asp Ile Arg Arg Trp Ser Lys Gly Glu Val Lys Lys Pro Glu
             20                  25                  30

Thr Ile Asn Tyr Arg Thr Leu Lys Pro Glu Lys Asp Gly Leu Phe Cys
         35                  40                  45
```

```
Glu Arg Ile Phe Gly Pro Thr Arg Asp Trp Glu Cys Ala Cys Gly Lys
 50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                 85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
    290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
    370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
        435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
```

-continued

```
            465                 470                 475                 480
        Pro Glu Val Trp Asp Val Leu Glu Ala Ile Ser Glu His Pro Val
                        485                 490                 495
        Met Leu Asn Arg Ala Pro Thr Leu His Arg Leu Gly Ile Gln Ala Phe
                    500                 505                 510
        Glu Pro Val Leu Val Glu Gly Lys Ala Ile Gln Leu His Pro Leu Ala
                    515                 520                 525
        Cys Glu Ala Phe Asn Ala Asp Phe Asp Gly Asp Gln Met Ala Val His
                    530                 535                 540
        Leu Pro Leu Ser Ala Glu Ala Gln Ala Glu Ala Arg Val Leu Met Leu
        545                 550                 555                 560
        Ala Ser Asn Asn Ile Leu Ser Pro Ala Ser Gly Lys Pro Leu Ala Met
                            565                 570                 575
        Pro Arg Leu Asp Met Val Thr Gly Leu Tyr Tyr Leu Thr Leu Glu Lys
                        580                 585                 590
        Ser Ser Glu Glu Phe Gly Gly Gln Gly Ala Tyr Gln Pro Ala Asp Glu
                    595                 600                 605
        Asn Gly Pro Glu Lys Gly Val Tyr Ser Ser Leu Ala Glu Ala Ile Met
                610                 615                 620
        Ala Tyr Asp Arg Gly Val Leu Gly Leu Gln Ala Pro Val Arg Ile Arg
        625                 630                 635                 640
        Leu Asn His Leu Arg Pro Pro Ala Glu Val Glu Ala Glu Gln Phe Pro
                            645                 650                 655
        Asp Gly Trp Asn Gln Gly Glu Thr Trp Leu Ala His Thr Thr Leu Gly
                        660                 665                 670
        Arg Val Met Phe Asn Glu Ile Leu Pro Trp Asn Tyr Pro Tyr Leu Glu
                    675                 680                 685
        Gly Val Met Val Arg Lys Gly Gly Ser Asp Lys Ile Met Leu Gly
                690                 695                 700
        Asp Val Val Asn Asp Leu Ala Ala Lys Tyr Pro Met Ile Thr Val Ala
        705                 710                 715                 720
        Gln Thr Met Asp Lys Met Lys Asp Ala Gly Phe Tyr Trp Ser Thr Arg
                        725                 730                 735
        Ser Gly Val Thr Ile Ala Met Ser Asp Val Leu Val Leu Pro Asn Lys
                    740                 745                 750
        Glu Glu Met Leu Asp Arg Tyr Glu Glu Ser Ala Arg Gln Ile Glu Val
                    755                 760                 765
        Lys Tyr Asn Arg Gly Lys Leu Thr Gly Arg Glu Arg Tyr Asp Arg Leu
                770                 775                 780
        Val Glu Leu Trp Lys Asp Ala Thr Asp Glu Val Gly Gln Ala Val Glu
        785                 790                 795                 800
        Asp Leu Tyr Pro Asp Asp Asn Pro Ile Pro Met Ile Val Lys Ser Gly
                        805                 810                 815
        Ala Ala Gly Asn Met Arg Gln Ile Trp Thr Leu Ala Gly Met Lys Gly
                    820                 825                 830
        Met Val Val Asn Ser Lys Gly Asp Tyr Ile Thr Arg Pro Ile Lys Thr
                    835                 840                 845
        Ser Phe Arg Glu Gly Leu Thr Val Leu Glu Tyr Phe Asn Asn Ser His
                850                 855                 860
        Gly Ser Arg Lys Gly Leu Ala Asp Thr Ala Leu Arg Thr Ala Asp Ser
        865                 870                 875                 880
        Gly Tyr Leu Thr Arg Arg Leu Val Asp Val Ala Gln Asp Val Ile Val
                        885                 890                 895
```

-continued

```
Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
            915                 920                 925

Asp Leu Ile Glu Thr Ser Val Ser Gly Arg Val Leu Ala Gly Asp Ala
            930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Ala Gly Ile Lys Asp Val Lys
            965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
            995                 1000                1005

Ala Val Gly Ile Val Ala Ala Gln Ser Ile Gly Glu Pro Gly Thr Gln
            1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
            1075                1080                1085

Asn Val Val Tyr Glu Lys Leu Ser Lys Arg Gln Gly Leu Ala Ser Thr
            1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
            1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
            1155                1160                1165

Ala Ile His Asp Lys His Ile Glu Ile Ile Arg Gln Met Leu Arg
            1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
            1220                1225                1230

Lys Ala Ser Leu Pro Thr Glu Ser Trp Leu Ser Ala Ala Ser Phe Gln
            1235                1240                1245

Glu Thr Thr Arg Val Leu Thr Asp Ala Ala Ile Asn Lys Arg Ser Asp
            1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
            1300                1305                1310
```

Ile Tyr Gly Asp Asp Gly Phe Gly Glu Phe Thr Gly Ala Ser Val Pro
        1315                1320                1325

Leu Asp Glu Ala Phe
    1330

<210> SEQ ID NO 17
<211> LENGTH: 1333
<212> TYPE: PRT
<213> ORGANISM: Artificial Sequence
<220> FEATURE:
<223> OTHER INFORMATION: RpoC of KCCM11016P-rpoC(M10)

<400> SEQUENCE: 17

Met Leu Asp Val Asn Val Phe Asp Glu Leu Arg Ile Gly Leu Ala Thr
 1               5                  10                  15

Ala Asp Asp Ile Arg Arg Trp Ser Lys Gly Glu Val Lys Lys Pro Glu
             20                  25                  30

Thr Ile Asn Tyr Arg Thr Leu Lys Pro Glu Lys Asp Gly Leu Phe Cys
         35                  40                  45

Glu Arg Ile Phe Gly Pro Thr Arg Asp Trp Glu Cys Ala Cys Gly Lys
     50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                 85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
    290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

-continued

```
Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
            355                 360                 365

Asn Glu Lys Arg Met Leu Gln Glu Ser Val Asp Ala Leu Phe Asp Asn
        370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
            405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
        450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
            530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
        610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685

Gly Val Met Val Arg Lys Gly Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
```

```
              755                 760                 765
Lys Tyr Asn Arg Gly Lys Leu Thr Gly Arg Glu Arg Tyr Asp Arg Leu
        770                 775                 780

Val Glu Leu Trp Lys Asp Ala Thr Asp Glu Val Gly Gln Ala Val Glu
785                 790                 795                 800

Asp Leu Tyr Pro Asp Asn Pro Ile Pro Met Ile Val Lys Ser Gly
                805                 810                 815

Ala Ala Gly Asn Met Arg Gln Ile Trp Thr Leu Ala Gly Met Lys Gly
                820                 825                 830

Met Val Val Asn Ser Lys Gly Asp Tyr Ile Thr Arg Pro Ile Lys Thr
                835                 840                 845

Ser Phe Arg Glu Gly Leu Thr Val Leu Glu Tyr Phe Asn Asn Ser His
    850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
                900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
    930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
                980                 985                 990

Cys Tyr Gly Lys Ser Met Ala Ser Gly Gln Gln Val Asp Ile Gly Glu
        995                 1000                1005

Ala Val Gly Ile Val Ala Ala Gln Ser Ile Gly Glu Pro Gly Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
        1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
            1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
        1155                1160                1165

Ala Ile His Asp Lys His Ile Glu Ile Ile Arg Gln Met Leu Arg
            1170                1175                1180
```

```
Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
        1220                1225                1230

Lys Ala Ser Leu Ala Thr Glu Ser Asn Leu Ser Ala Ala Ser Phe Gln
    1235                1240                1245

Glu Thr Thr Arg Val Leu Thr Asp Ala Ala Ile Asn Lys Arg Ser Asp
1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
    1315                1320                1325

Leu Asp Glu Ala Phe
    1330

<210> SEQ ID NO 18
<211> LENGTH: 1333
<212> TYPE: PRT
<213> ORGANISM: Artificial Sequence
<220> FEATURE:
<223> OTHER INFORMATION: RpoC of KCCM11016P-rpoC(M11)

<400> SEQUENCE: 18

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Phe Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Ala Asp Lys Glu Met Gln His Ile
        195                 200                 205
```

-continued

Arg Glu Arg Ala Gln Arg Glu Ile Asp Arg Leu Asp Glu Val Trp Gln
            210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
            275                 280                 285

Lys Met Arg Ala Leu Lys Arg Leu Lys Val Val Ala Ala Phe Gln Arg
            290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
            355                 360                 365

Asn Glu Lys Arg Met Leu Gln Glu Ser Val Asp Ala Leu Phe Asp Asn
            370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
            450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
            530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
            610                 615                 620

-continued

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
            645                 650                 655

Asp Gly Trp Asn Gln Gly Glu Thr Trp Leu Ala His Thr Thr Leu Gly
        660                 665                 670

Arg Val Met Phe Asn Glu Ile Leu Pro Trp Asn Tyr Pro Tyr Leu Glu
    675                 680                 685

Gly Val Met Val Arg Lys Gly Gly Ser Asp Lys Ile Met Leu Gly
690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
        755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
        995                 1000                1005

Ala Val Gly Ile Val Ala Ala Gln Ser Ile Gly Glu Pro Gly Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys

Asn Cys Ala Pro Ile Ala Ser Val Glu Gly Val Ile His Leu Glu Asp
           1045                1050                1055

Glu Gly Asn Phe Tyr Thr Leu Thr Ile Val Pro Asp Asp Gly Ser Asp
        1060                1065                1070

Asn Val Val Tyr Glu Lys Leu Ser Lys Arg Gln Gly Leu Ala Ser Thr
    1075                1080                1085

Arg Val Ala Met Glu Ser Asn Ala Gly Ala Phe Ile Glu Arg Thr Leu
1090                1095                1100

Thr Glu Gly Asp Arg Val Thr Val Gly Gln Arg Leu Leu Arg Gly Ala
1105                1110                1115                1120

Ala Asp Pro His Asp Val Leu Glu Ile Leu Gly Arg Arg Gly Val Glu
        1125                1130                1135

Gln His Leu Ile Asp Glu Val Gln Ala Val Tyr Arg Ala Gln Gly Val
    1140                1145                1150

Ala Ile His Asp Lys His Ile Glu Ile Ile Arg Gln Met Leu Arg
1155                1160                1165

Arg Gly Thr Val Ile Glu Ser Gly Ser Thr Glu Phe Leu Pro Gly Ser
        1170                1175                1180

Leu Val Asp Leu Ser Glu Ala Lys Leu Ala Asn Ser Glu Ala Ile Gly
1185                1190                1195                1200

Ala Gly Gly Gln Pro Ala Glu Leu Arg Ser Glu Ile Met Gly Ile Thr
        1205                1210                1215

Lys Ala Ser Leu Ala Thr Glu Ser Trp Leu Ser Ala Ala Ser Phe Gln
    1220                1225                1230

Glu Thr Thr Arg Val Leu Cys Asp Ala Ala Ile Asn Lys Arg Ser Asp
1235                1240                1245

Lys Leu Ile Gly Leu Lys Glu Asn Val Ile Ile Gly Lys Leu Ile Pro
1250                1255                1260

Ala Gly Thr Gly Ile Ser Arg Tyr Arg Asn Ile Ser Ile Lys Pro Thr
        1265                1270                1275                1280

Glu Ala Ala Arg Asn Ala Ala Tyr Ser Ile Pro Thr Tyr Gly Glu Ser
    1285                1290                1295

Ile Tyr Gly Asp Asp Gly Phe Gly Glu Phe Thr Gly Ala Ser Val Pro
        1300                1305                1310

Leu Asp Glu Ala Phe
    1315                1320                1325

<210> SEQ ID NO 19
<211> LENGTH: 1333
<212> TYPE: PRT
<213> ORGANISM: Artificial Sequence
<220> FEATURE:
<223> OTHER INFORMATION: RpoC of KCCM11016P-rpoC(M12)

<400> SEQUENCE: 19

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Phe Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val

```
                65                  70                  75                  80
Glu Val Thr Lys Ser Lys Val Arg Arg Glu Arg Met Gly His Ile Glu
                    85                  90                  95
Leu Ala Ala Pro Val Thr His Ile Trp Tyr Phe Lys Gly Val Pro Ser
                    100                 105                 110
Arg Leu Gly Tyr Leu Leu Asp Leu Ala Pro Lys Asp Leu Asp Leu Ile
                    115                 120                 125
Ile Tyr Phe Gly Ala Asn Ile Ile Thr Ser Val Asp Glu Glu Ala Arg
            130                 135                 140
His Ser Asp Gln Thr Thr Leu Glu Ala Glu Met Leu Leu Glu Lys Lys
145                 150                 155                 160
Asp Val Glu Ala Asp Ala Glu Ser Asp Ile Ala Glu Arg Ala Glu Lys
                    165                 170                 175
Leu Glu Glu Asp Leu Ala Glu Leu Glu Ala Ala Gly Ala Lys Ala Asp
                    180                 185                 190
Ala Arg Arg Lys Val Gln Ala Ala Asp Lys Glu Met Gln His Ile
                    195                 200                 205
Arg Glu Arg Ala Gln Arg Glu Ile Asp Arg Leu Asp Glu Val Trp Gln
            210                 215                 220
Thr Phe Ile Lys Leu Ala Pro Lys Gln Met Ile Arg Asp Glu Lys Leu
225                 230                 235                 240
Tyr Asp Glu Leu Ile Asp Arg Tyr Glu Asp Tyr Phe Thr Gly Gly Met
                    245                 250                 255
Gly Ala Glu Ser Ile Glu Ala Leu Ile Gln Asn Phe Asp Leu Asp Ala
                    260                 265                 270
Glu Ala Glu Glu Leu Arg Asp Ile Ile Asn Asn Gly Lys Gly Gln Lys
                    275                 280                 285
Lys Met Arg Ala Leu Lys Arg Leu Lys Val Val Ala Ala Phe Gln Arg
            290                 295                 300
Ser Gly Asn Asp Pro Ala Gly Met Val Leu Asn Ala Ile Pro Val Ile
305                 310                 315                 320
Pro Pro Glu Leu Arg Pro Met Val Gln Leu Asp Gly Gly Arg Phe Ala
                    325                 330                 335
Thr Ser Asp Leu Asn Asp Leu Tyr Arg Arg Val Ile Asn Arg Asn Asn
                    340                 345                 350
Arg Leu Lys Arg Met Ile Glu Leu Gly Ala Pro Glu Ile Ile Val Asn
                    355                 360                 365
Asn Glu Lys Arg Met Leu Gln Glu Ser Val Asp Ala Leu Phe Asp Asn
            370                 375                 380
Gly Arg Arg Gly Arg Pro Val Thr Gly Pro Gly Asn Arg Pro Leu Lys
385                 390                 395                 400
Ser Leu Ser Asp Leu Leu Lys Gly Lys Gln Gly Arg Phe Arg Gln Asn
                    405                 410                 415
Leu Leu Gly Lys Arg Val Asp Tyr Ser Gly Arg Ser Val Ile Ile Val
                    420                 425                 430
Gly Pro Gln Leu Arg Leu His Glu Cys Gly Leu Pro Lys Leu Met Ala
                    435                 440                 445
Leu Glu Leu Phe Lys Pro Phe Val Met Lys Arg Leu Val Glu Asn Glu
                    450                 455                 460
Tyr Ala Gln Asn Ile Lys Ser Ala Lys Arg Met Val Glu Arg Gln Arg
465                 470                 475                 480
Pro Glu Val Trp Asp Val Leu Glu Glu Ala Ile Ser Glu His Pro Val
                    485                 490                 495
```

-continued

```
Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
            610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685

Gly Val Met Val Arg Lys Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
            835                 840                 845

Ser Phe Arg Glu Gly Leu Thr Val Leu Glu Tyr Phe Asn Asn Ser His
            850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910
```

-continued

```
Ala Glu Val Leu Asp Ala Thr Gly Ala Val Thr Gly Tyr Thr Arg His
            915                 920                 925

Asp Leu Ile Glu Thr Ser Val Ser Gly Arg Val Leu Ala Gly Asp Ala
        930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
        995                 1000                1005

Ala Val Gly Ile Val Ala Ala Gln Ser Ile Gly Glu Pro Gly Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
        1060                1065                1070

Glu Gly Asn Phe Tyr Thr Leu Thr Ile Val Pro Asp Asp Gly Ser Asp
    1075                1080                1085

Asn Val Val Tyr Glu Lys Leu Ser Lys Arg Gln Gly Leu Ala Ser Thr
1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
            1125                1130                1135

Ala Asp Pro His Asp Val Leu Glu Ile Leu Gly Arg Arg Gly Val Glu
        1140                1145                1150

Gln His Leu Ile Asp Glu Val Gln Ala Val Tyr Arg Ala Gln Gly Val
    1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
        1220                1225                1230

Lys Ala Ser Leu Ala Thr Glu Ser Trp Leu Ser Ala Ala Ser Phe Gln
    1235                1240                1245

Tyr Thr Thr Arg Val Leu Thr Asp Ala Ala Ile Asn Lys Arg Ser Asp
    1250                1255                1260

Lys Leu Ile Gly Leu Lys Glu Asn Val Ile Gly Lys Leu Ile Pro
1265                1270                1275                1280

Ala Phe Thr Gly Ile Ser Arg Tyr Arg Asn Ile Ser Ile Lys Pro Thr
        1285                1290                1295

Glu Ala Ala Arg Asn Ala Ala Tyr Ser Ile Pro Thr Tyr Gly Glu Ser
            1300                1305                1310

Ile Tyr Gly Asp Asp Gly Phe Gly Glu Phe Thr Gly Ala Ser Val Pro
    1315                1320                1325

Leu Asp Glu Ala Phe
```

<210> SEQ ID NO 20
<211> LENGTH: 1333
<212> TYPE: PRT
<213> ORGANISM: Artificial Sequence
<220> FEATURE:
<223> OTHER INFORMATION: RpoC of KCCM11016P-rpoC(M13)

<400> SEQUENCE: 20

```
Met Leu Asp Val Asn Val Phe Asp Glu Leu Arg Ile Gly Leu Ala Thr
  1               5                  10                  15

Ala Asp Asp Ile Arg Arg Trp Ser Lys Gly Glu Val Lys Lys Pro Glu
             20                  25                  30

Thr Ile Asn Tyr Arg Thr Leu Lys Pro Glu Lys Asp Gly Leu Phe Cys
         35                  40                  45

Glu Arg Ile Phe Gly Pro Thr Arg Asp Trp Glu Cys Ala Cys Gly Lys
     50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                 85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
    290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
```

-continued

```
              355                 360                 365
Asn Glu Lys Arg Met Leu Gln Glu Ser Val Asp Ala Leu Phe Asp Asn
    370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
            530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
            610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685

Gly Val Met Val Arg Lys Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
            770                 775                 780
```

-continued

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
            805                 810                 815

Ala Ala Gly Asn Met Arg Gln Ile Trp Thr Leu Ala Gly Met Lys Gly
        820                 825                 830

Met Val Val Asn Ser Lys Gly Asp Tyr Ile Thr Arg Pro Ile Lys Thr
    835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
        995                 1000                1005

Ala Val Gly Ile Val Ala Ala Gln Ser Ile Gly Glu Pro Ser Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
                1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
        1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
        1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
                1205                1210                1215

Ala Gly Gly Gln Pro Ala Glu Leu Arg Ser Glu Ile Met Gly Ile Thr
        1220                1225                1230

Lys Ala Ser Leu Ala Thr Glu Ser Trp Leu Ser Ala Ala Ser Phe Gln
        1235                1240                1245

Glu Thr Thr Arg Val Leu Thr Asp Ala Ala Ile Asn Lys Arg Ser Asp
    1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
    1315                1320                1325

Leu Asp Glu Ala Phe
    1330

<210> SEQ ID NO 21
<211> LENGTH: 1333
<212> TYPE: PRT
<213> ORGANISM: Artificial Sequence
<220> FEATURE:
<223> OTHER INFORMATION: RpoC of KCCM11016P-rpoC(M14)

<400> SEQUENCE: 21

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

-continued

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
    290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
        435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
    530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
    610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro

-continued

```
                645                 650                 655
Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685

Gly Val Met Val Arg Lys Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
            725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
            770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
            835                 840                 845

Ser Phe Arg Glu Gly Leu Thr Val Leu Glu Tyr Phe Asn Asn Ser His
            850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
            915                 920                 925

Asp Leu Ile Glu Thr Ser Val Ser Gly Arg Val Leu Ala Gly Asp Ala
            930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
            995                 1000                1005

Ala Val Gly Ile Val Ala Ala Gln Ser Ile Gly Glu Pro Gly Thr Gln
   1010                1015                1020

Leu Thr Met Arg Thr Phe His Gln Gly Val Gly Gly Asp Ile Thr
1025                1030                1035                1040

Gly Gly Leu Pro Arg Val Gln Glu Leu Phe Glu Ala Arg Val Pro Lys
                1045                1050                1055

Asn Cys Ala Pro Ile Ala Ser Val Glu Gly Val Ile His Leu Glu Asp
            1060                1065                1070
```

-continued

Glu Gly Asn Phe Tyr Thr Leu Thr Ile Val Pro Asp Asp Gly Ser Asp
            1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
            1155                1160                1165

Ala Ile His Asp Lys His Ile Glu Ile Ile Arg Gln Met Leu Arg
        1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
                1220                1225                1230

Lys Ala Ser Leu Ala Thr Glu Ser Trp Leu Gly Ala Ala Ser Phe Gln
        1235                1240                1245

Glu Thr Thr Arg Val Leu Thr Asp Ala Ala Ile Asn Lys Arg Ser Asp
            1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
                1285                1290                1295

Glu Ala Ala Arg Asn Ala Ala Tyr Ser Ile Pro Thr Tyr Gly Glu Ser
                1300                1305                1310

Ile Tyr Gly Asp Asp Gly Phe Gly Glu Phe Thr Gly Ala Ser Val Pro
        1315                1320                1325

Leu Asp Glu Ala Phe
    1330

<210> SEQ ID NO 22
<211> LENGTH: 1333
<212> TYPE: PRT
<213> ORGANISM: Artificial Sequence
<220> FEATURE:
<223> OTHER INFORMATION: RpoC of KCCM11016P-rpoC(M15)

<400> SEQUENCE: 22

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
                20                  25                  30

Thr Ile Asn Tyr Arg Thr Leu Lys Pro Glu Lys Asp Gly Leu Phe Cys
            35                  40                  45

Glu Arg Ile Phe Gly Pro Thr Arg Asp Trp Glu Cys Ala Cys Gly Lys
        50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

```
Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
            115                 120                 125

Ile Tyr Phe Gly Ala Asn Ile Ile Thr Ser Val Asp Glu Glu Ala Arg
            130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
            195                 200                 205

Arg Glu Arg Ala Gln Arg Glu Ile Asp Arg Leu Asp Glu Val Trp Gln
            210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
            275                 280                 285

Lys Met Arg Ala Leu Lys Arg Leu Lys Val Val Ala Ala Phe Gln Arg
290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Arg Phe Ala
            325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
            355                 360                 365

Asn Glu Lys Arg Met Leu Gln Glu Ser Val Asp Ala Leu Phe Asp Asn
            370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
            450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510
```

-continued

Glu Pro Val Leu Val Glu Gly Lys Ala Ile Gln Leu His Pro Leu Ala
515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
    610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
        675                 680                 685

Gly Val Met Val Arg Lys Gly Gly Ser Asp Lys Ile Met Leu Gly
    690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
        755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
            820                 825                 830

Met Val Val Asn Ser Lys Gly Asp Tyr Ile Thr Arg Pro Ile Lys Thr
        835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
                865                 870                 875                 880

Gly Tyr Leu Thr Arg Arg Leu Val Asp Val Ala Gln Asp Val Ile Val
            885                 890                 895

Arg Val Glu Asp Cys Gly Thr Arg Gln Gly Val Arg Val Pro Val Ala
        900                 905                 910

Ala Glu Val Leu Asp Ala Thr Gly Ala Val Thr Gly Tyr Thr Arg His
    915                 920                 925

Asp Leu Ile Glu Thr Ser Val Ser Gly Arg Val Leu Ala Gly Asp Ala

```
            930                 935                 940
Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
                980                 985                 990

Cys Tyr Gly Lys Ser Met Ala Ser Gly Gln Gln Val Asp Ile Gly Glu
                995                1000                1005

Ala Val Gly Ile Val Ala Ala Gln Ser Ile Gly Glu Pro Gly Thr Gln
               1010                1015                1020

Leu Thr Met Arg Thr Phe His Gln Gly Val Gly Gly Asp Ile Thr
1025                1030                1035                1040

Gly Gly Leu Pro Arg Val Gln Glu Leu Phe Glu Ala Arg Val Pro Lys
               1045                1050                1055

Asn Cys Ala Pro Ile Ala Ser Val Glu Gly Val Ile His Leu Glu Asp
               1060                1065                1070

Glu Gly Asn Phe Tyr Thr Leu Thr Ile Val Pro Asp Asp Gly Ser Asp
               1075                1080                1085

Asn Val Val Tyr Glu Lys Leu Ser Lys Arg Gln Gly Leu Ala Ser Thr
               1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
               1125                1130                1135

Ala Asp Pro His Asp Val Leu Glu Ile Leu Gly Arg Arg Gly Val Glu
               1140                1145                1150

Gln His Leu Ile Asp Glu Val Gln Ala Val Tyr Arg Ala Gln Gly Val
               1155                1160                1165

Ala Ile His Asp Lys His Ile Glu Ile Ile Arg Gln Met Leu Arg
               1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
               1205                1210                1215

Ala Gly Gly Gln Pro Ala Glu Leu Arg Ser Glu Ile Met Gly Ile Thr
               1220                1225                1230

Lys Ala Ser Leu Ala Thr Thr Ser Trp Leu Ser Ala Ala Ser Phe Gln
               1235                1240                1245

Glu Thr Thr Arg Val Leu Thr Asp Ala Ala Ile Asn Lys Arg Ser Asp
               1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
               1285                1290                1295

Glu Ala Ala Arg Asn Ala Ala Tyr Ser Ile Pro Thr Tyr Gly Glu Ser
               1300                1305                1310

Ile Tyr Gly Asp Asp Gly Phe Gly Glu Phe Thr Gly Ala Ser Val Pro
               1315                1320                1325

Leu Asp Glu Ala Phe
   1330

<210> SEQ ID NO 23
```

```
<211> LENGTH: 1333
<212> TYPE: PRT
<213> ORGANISM: Artificial Sequence
<220> FEATURE:
<223> OTHER INFORMATION: RpoC of KCCM11016P-rpoC(M16)

<400> SEQUENCE: 23
```

| | | | | | | | | | | | | | | |
|---|---|---|---|---|---|---|---|---|---|---|---|---|---|---|
|Met|Leu|Asp|Val|Asn|Val|Phe|Asp|Glu|Leu|Arg|Ile|Gly|Leu|Ala|Thr|
|1| | | |5| | | | |10| | | | |15|

| | | | | | | | | | | | | | | |
|---|---|---|---|---|---|---|---|---|---|---|---|---|---|---|
|Ala|Asp|Asp|Ile|Arg|Arg|Trp|Ser|Lys|Gly|Glu|Val|Lys|Lys|Pro|Glu|
| | | |20| | | | |25| | | | |30| | |

Thr Ile Asn Tyr Arg Thr Leu Lys Pro Glu Lys Asp Gly Leu Phe Cys
            35                  40                  45

Glu Arg Ile Phe Gly Pro Thr Arg Asp Trp Glu Cys Ala Cys Gly Lys
 50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                 85                  90                  95

Leu Ala Ala Pro Val Thr His Ile Trp Tyr Phe Lys Gly Val Pro Ser
                100                 105                 110

Arg Leu Gly Tyr Leu Leu Asp Leu Ala Pro Lys Asp Leu Asp Leu Ile
                115                 120                 125

Ile Tyr Phe Gly Ala Asn Ile Ile Thr Ser Val Asp Glu Glu Ala Arg
130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
                180                 185                 190

Ala Arg Arg Lys Val Gln Ala Ala Asp Lys Glu Met Gln His Ile
                195                 200                 205

Arg Glu Arg Ala Gln Arg Glu Ile Asp Arg Leu Asp Glu Val Trp Gln
210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
                260                 265                 270

Glu Ala Glu Glu Leu Arg Asp Ile Ile Asn Asn Gly Lys Gly Gln Lys
                275                 280                 285

Lys Met Arg Ala Leu Lys Arg Leu Lys Val Val Ala Ala Phe Gln Arg
290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
                340                 345                 350

Arg Leu Lys Arg Met Ile Glu Leu Gly Ala Pro Glu Ile Ile Val Asn
                355                 360                 365

Asn Glu Lys Arg Met Leu Gln Glu Ser Val Asp Ala Leu Phe Asp Asn
                370                 375                 380

```
Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
            405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
            485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
            515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
            565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
            610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
            645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685

Gly Val Met Val Arg Lys Gly Gly Ser Asp Lys Ile Met Leu Gly
            690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
            725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
            770                 775                 780

Val Glu Leu Trp Lys Asp Ala Thr Asp Glu Val Gly Gln Ala Val Glu
785                 790                 795                 800
```

```
Asp Leu Tyr Pro Asp Asp Asn Pro Ile Pro Met Ile Val Lys Ser Gly
            805                 810                 815

Ala Ala Gly Asn Met Arg Gln Ile Trp Thr Leu Ala Gly Met Lys Gly
        820                 825                 830

Met Val Val Asn Ser Lys Gly Asp Tyr Ile Thr Arg Pro Ile Lys Thr
    835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
            900                 905                 910

Ala Glu Val Leu Asp Ala Thr Gly Ala Val Thr Gly Tyr Thr Arg His
        915                 920                 925

Asp Leu Ile Glu Thr Ser Val Ser Gly Arg Val Leu Ala Gly Asp Ala
    930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
        995                 1000                1005

Ala Val Gly Ile Val Ala Ala Gln Ser Ile Gly Glu Pro Gly Thr Gln
    1010                1015                1020

Leu Thr Met Arg Thr Phe His Gln Gly Lys Val Gly His Ile Thr
1025                1030                1035                1040

Gly Gly Leu Pro Arg Val Gln Glu Leu Phe Glu Ala Arg Val Pro Lys
                1045                1050                1055

Asn Cys Ala Pro Ile Ala Ser Val Glu Gly Val Ile His Leu Glu Asp
            1060                1065                1070

Glu Gly Asn Phe Tyr Thr Leu Thr Ile Val Pro Asp Asp Gly Ser Asp
        1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
        1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
                1205                1210                1215

Ala Gly Gly Gln Pro Ala Glu Leu Arg Ser Glu Ile Met Gly Ile Thr
```

```
                    1220                1225                1230
Lys Ala Ser Leu Ala Thr Glu Ser Trp Leu Ser Ala Ala Ser Phe Gln
        1235                1240                1245

Glu Thr Thr Arg Val Leu Thr Asp Ala Ala Ile Asn Lys Arg Ser Asp
    1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
    1315                1320                1325

Leu Asp Glu Ala Phe
    1330

<210> SEQ ID NO 24
<211> LENGTH: 1333
<212> TYPE: PRT
<213> ORGANISM: Artificial Sequence
<220> FEATURE:
<223> OTHER INFORMATION: RpoC of KCCM11016P-rpoC(M17)

<400> SEQUENCE: 24

Met Leu Asp Val Asn Val Phe Asp Glu Leu Arg Ile Gly Leu Ala Thr
  1               5                  10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
```

```
                     245                 250                 255
Gly Ala Glu Ser Ile Glu Ala Leu Ile Gln Asn Phe Asp Leu Asp Ala
                260                 265                 270

Glu Ala Glu Glu Leu Arg Asp Ile Ile Asn Asn Gly Lys Gly Gln Lys
            275                 280                 285

Lys Met Arg Ala Leu Lys Arg Leu Lys Val Val Ala Ala Phe Gln Arg
        290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Arg Phe Ala
                325                 330                 335

Thr Ser Asp Glu Asn Asp Leu Tyr Arg Arg Val Ile Asn Arg Asn Asn
                340                 345                 350

Arg Leu Lys Arg Met Ile Glu Leu Gly Ala Pro Glu Ile Ile Val Asn
            355                 360                 365

Asn Glu Lys Arg Met Leu Gln Glu Ser Val Asp Ala Leu Phe Asp Asn
        370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
        435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
    530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
    610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670
```

```
Arg Val Met Phe Asn Glu Ile Leu Pro Trp Asn Tyr Pro Tyr Leu Glu
    675                 680                 685

Gly Val Met Val Arg Lys Gly Gly Ser Asp Lys Ile Met Leu Gly
690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
                740                 745                 750

Glu Glu Met Leu Asp Arg Tyr Glu Glu Ser Ala Arg Gln Ile Glu Val
                755                 760                 765

Lys Tyr Asn Arg Gly Lys Leu Thr Gly Arg Glu Arg Tyr Asp Arg Leu
                770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
                820                 825                 830

Met Val Val Asn Ser Lys Gly Asp Tyr Ile Thr Arg Pro Ile Lys Thr
    835                 840                 845

Ser Phe Arg Glu Gly Leu Thr Val Leu Glu Tyr Phe Asn Asn Ser His
    850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
                900                 905                 910

Ala Glu Val Leu Asp Ala Thr Gly Ala Val Thr Gly Tyr Thr Arg His
    915                 920                 925

Asp Leu Ile Glu Thr Ser Val Ser Gly Arg Val Leu Ala Gly Asp Ala
    930                 935                 940

Thr Asn Ala Ala Gly Glu Val Val Leu Ala Ala Gly Thr Asp Leu Thr
945                 950                 955                 960

Glu Leu Asn Ile Asp Leu Leu Val Glu Ala Gly Ile Lys Asp Val Lys
                965                 970                 975

Val Arg Ser Val Leu Thr Cys Gln Thr Pro Thr Gly Val Cys Ala Lys
                980                 985                 990

Cys Tyr Gly Lys Ser Met Ala Ser Gly Gln Gln Val Asp Ile Gly Glu
    995                 1000                1005

Ala Val Gly Ile Val Asp Ala Gln Ser Ile Gly Glu Pro Gly Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
                1045                1050                1055

Asn Cys Ala Pro Ile Ala Ser Val Glu Gly Val Ile His Leu Glu Asp
                1060                1065                1070

Glu Gly Asn Phe Tyr Thr Leu Thr Ile Val Pro Asp Asp Gly Ser Asp
                1075                1080                1085
```

Asn Val Val Tyr Glu Lys Leu Ser Lys Arg Gln Gly Leu Ala Ser Thr
1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
        1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
                1205                1210                1215

Ala Gly Gly Gln Pro Ala Glu Leu Arg Ser Glu Ile Met Gly Ile Thr
            1220                1225                1230

Lys Ala Ser Leu Ala Thr Glu Ser Trp Leu Ser Ala Ala Ser Phe Gln
        1235                1240                1245

Glu Thr Thr Arg Val Leu Thr Asp Ala Ala Ile Asn Lys Arg Ser Asp
    1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
                1285                1290                1295

Glu Ala Ala Arg Asn Ala Ala Tyr Ser Ile Pro Thr Tyr Gly Glu Ser
            1300                1305                1310

Ile Tyr Gly Asp Asp Gly Phe Gly Glu Phe Thr Gly Ala Ser Val Pro
        1315                1320                1325

Leu Asp Glu Ala Phe
    1330

<210> SEQ ID NO 25
<211> LENGTH: 1333
<212> TYPE: PRT
<213> ORGANISM: Artificial Sequence
<220> FEATURE:
<223> OTHER INFORMATION: RpoC of KCCM11016P-rpoC(M18)

<400> SEQUENCE: 25

Met Leu Asp Val Asn Val Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

```
Arg Leu Gly Tyr Leu Leu Asp Leu Ala Pro Lys Asp Leu Asp Leu Ile
            115                 120                 125
Ile Tyr Phe Gly Ala Asn Ile Ile Thr Ser Val Asp Glu Glu Ala Arg
130                 135                 140
His Ser Asp Gln Thr Thr Leu Glu Ala Glu Met Leu Leu Glu Lys Lys
145                 150                 155                 160
Asp Val Glu Ala Asp Ala Glu Ser Asp Ile Ala Glu Arg Ala Glu Lys
                165                 170                 175
Leu Glu Glu Asp Leu Ala Glu Leu Glu Ala Ala Gly Ala Lys Ala Asp
            180                 185                 190
Ala Arg Arg Lys Val Gln Ala Ala Asp Lys Glu Met Gln His Ile
        195                 200                 205
Arg Glu Arg Ala Gln Arg Glu Ile Asp Arg Leu Asp Glu Val Trp Gln
210                 215                 220
Thr Phe Ile Lys Leu Ala Pro Lys Gln Met Ile Arg Asp Glu Lys Leu
225                 230                 235                 240
Tyr Asp Glu Leu Ile Asp Arg Tyr Glu Asp Tyr Phe Thr Gly Gly Met
                245                 250                 255
Gly Ala Glu Ser Ile Glu Ala Leu Ile Gln Asn Phe Asp Leu Asp Ala
            260                 265                 270
Glu Ala Glu Glu Leu Arg Asp Ile Ile Asn Asn Gly Lys Gly Gln Lys
        275                 280                 285
Lys Met Arg Ala Leu Lys Arg Leu Lys Val Val Ala Ala Phe Gln Arg
290                 295                 300
Ser Gly Asn Asp Pro Ala Gly Met Val Leu Asn Ala Ile Pro Val Ile
305                 310                 315                 320
Pro Pro Glu Leu Arg Pro Met Val Gln Leu Asp Gly Gly Arg Phe Ala
                325                 330                 335
Thr Ser Asp Leu Asn Asp Leu Tyr Arg Arg Val Ile Asn Arg Asn Asn
            340                 345                 350
Arg Leu Lys Arg Met Ile Glu Leu Gly Ala Pro Glu Ile Ile Val Asn
        355                 360                 365
Asn Glu Lys Arg Met Leu Gln Glu Ser Val Asp Ala Leu Phe Asp Asn
370                 375                 380
Gly Arg Arg Gly Arg Pro Val Thr Gly Pro Gly Asn Arg Pro Leu Lys
385                 390                 395                 400
Ser Leu Ser Asp Leu Leu Lys Gly Lys Gln Gly Arg Phe Arg Gln Asn
                405                 410                 415
Leu Leu Gly Lys Arg Val Asp Tyr Ser Gly Arg Ser Val Ile Ile Val
            420                 425                 430
Gly Pro Gln Leu Arg Leu His Glu Cys Gly Leu Pro Lys Leu Met Ala
        435                 440                 445
Leu Glu Leu Phe Lys Pro Phe Val Met Lys Arg Leu Val Glu Asn Glu
450                 455                 460
Tyr Ala Gln Asn Ile Lys Ser Ala Lys Arg Met Val Glu Arg Gln Arg
465                 470                 475                 480
Pro Glu Val Trp Asp Val Leu Glu Glu Ala Ile Ser Glu His Pro Val
                485                 490                 495
Met Leu Asn Arg Ala Pro Thr Leu His Arg Leu Gly Ile Gln Ala Phe
            500                 505                 510
Glu Pro Val Leu Val Glu Gly Lys Ala Ile Gln Leu His Pro Leu Ala
        515                 520                 525
Cys Glu Ala Phe Asn Ala Asp Phe Asp Gly Asp Gln Met Ala Val His
```

```
                530             535             540
Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
                580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
        610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
                660                 665                 670

Arg Val Met Phe Asn Glu Ile Leu Pro Trp Asn Tyr Pro Tyr Leu Glu
                675                 680                 685

Gly Val Met Val Arg Lys Gly Gly Ser Asp Lys Ile Met Leu Gly
690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
                740                 745                 750

Glu Glu Met Leu Asp Arg Tyr Glu Glu Ser Ala Arg Gln Ile Glu Val
                755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
                820                 825                 830

Met Val Val Asn Ser Lys Gly Asp Tyr Ile Thr Arg Pro Ile Lys Thr
                835                 840                 845

Ser Phe Arg Glu Gly Leu Thr Val Leu Glu Tyr Phe Asn Asn Ser His
850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
                885                 890                 895

Arg Val Glu Asp Cys Gly Thr Arg Gln Gly Val Arg Val Pro Val Ala
                900                 905                 910

Ala Glu Val Leu Asp Ala Thr Gly Ala Val Thr Gly Tyr Thr Arg His
                915                 920                 925

Asp Leu Ile Glu Thr Ser Val Ser Gly Arg Val Leu Ala Gly Asp Ala
                930                 935                 940

Thr Asn Ala Ala Gly Glu Val Val Leu Ala Ala Gly Thr Asp Leu Thr
945                 950                 955                 960
```

```
Glu Leu Asn Ile Asp Leu Leu Val Glu Ala Gly Ile Lys Asp Val Lys
            965                 970                 975

Val Arg Ser Val Leu Thr Cys Gln Thr Pro Thr Gly Val Cys Ala Lys
        980                 985                 990

Cys Tyr Gly Lys Ser Met Ala Ser Gly Gln Gln Val Asp Ile Gly Glu
    995                1000                1005

Ala Val Gly Ile Val Ala His Gln Ser Ile Gly Glu Pro Gly Thr Gln
1010                1015                1020

Leu Thr Met Arg Thr Phe His Gln Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
        1060                1065                1070

Glu Gly Asn Phe Tyr Thr Leu Thr Ile Val Pro Asp Asp Gly Ser Asp
    1075                1080                1085

Asn Val Val Tyr Glu Lys Leu Ser Lys Arg Gln Gly Leu Ala Ser Thr
1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
            1125                1130                1135

Ala Asp Pro His Asp Val Leu Glu Ile Leu Gly Arg Arg Gly Val Glu
        1140                1145                1150

Gln His Leu Ile Asp Glu Val Gln Ala Val Tyr Arg Ala Gln Gly Val
    1155                1160                1165

Ala Ile His Asp Lys His Ile Glu Ile Ile Arg Gln Met Leu Arg
1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
            1205                1210                1215

Ala Gly Gly Gln Pro Ala Glu Leu Arg Ser Glu Ile Met Gly Ile Thr
        1220                1225                1230

Lys Ala Ser Leu Ala Thr Glu Ser Trp Leu Ser Ala Ala Ser Phe Gln
    1235                1240                1245

Glu Thr Thr Arg Val Leu Thr Asp Ala Ala Ile Asn Lys Arg Ser Asp
1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
    1315                1320                1325

Leu Asp Glu Ala Phe
    1330

<210> SEQ ID NO 26
<211> LENGTH: 1333
<212> TYPE: PRT
<213> ORGANISM: Artificial Sequence
<220> FEATURE:
```

<223> OTHER INFORMATION: RpoC of KCCM11016P-rpoC(M19)

<400> SEQUENCE: 26

```
Met Leu Asp Val Asn Val Phe Asp Glu Leu Arg Ile Gly Leu Ala Thr
  1               5                  10                  15

Ala Asp Asp Ile Arg Arg Trp Ser Lys Gly Glu Val Lys Lys Pro Glu
             20                  25                  30

Thr Ile Asn Tyr Arg Thr Leu Lys Pro Glu Lys Asp Gly Leu Phe Cys
         35                  40                  45

Glu Arg Ile Phe Gly Pro Thr Arg Asp Trp Glu Cys Ala Cys Gly Lys
     50                  55                  60

Tyr Lys Arg Val Arg Tyr Lys Gly Ile Ile Cys Glu Arg Cys Gly Val
 65                  70                  75                  80

Glu Val Thr Lys Ser Lys Val Arg Arg Glu Arg Met Gly His Ile Glu
                 85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

Glu Ala Glu Glu Leu Arg Asp Ile Ile Asn Asn Gly Lys Gly Gln Lys
        275                 280                 285

Lys Met Arg Ala Leu Lys Arg Leu Lys Val Val Ala Ala Phe Gln Arg
    290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
    370                 375                 380

Gly Arg Arg Gly Arg Pro Val Thr Gly Pro Gly Asn Arg Pro Leu Lys
385                 390                 395                 400
```

```
Ser Leu Ser Asp Leu Leu Lys Gly Lys Gln Gly Arg Phe Arg Gln Asn
            405                 410                 415

Leu Leu Gly Lys Arg Val Asp Tyr Ser Gly Arg Ser Val Ile Ile Val
        420                 425                 430

Gly Pro Gln Leu Arg Leu His Glu Cys Gly Leu Pro Lys Leu Met Ala
        435                 440                 445

Leu Glu Leu Phe Lys Pro Phe Val Met Lys Arg Leu Val Glu Asn Glu
    450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
                565                 570                 575

Pro Arg Leu Asp Met Val Thr Gly Leu Tyr Tyr Leu Thr Leu Glu Lys
                580                 585                 590

Ser Ser Glu Glu Phe Gly Gly Gln Gly Ala Tyr Gln Pro Ala Asp Glu
            595                 600                 605

Asn Gly Pro Glu Lys Gly Val Tyr Ser Ser Leu Ala Glu Ala Ile Met
        610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
                645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
        675                 680                 685

Gly Val Met Val Arg Lys Gly Gly Ser Asp Lys Ile Met Leu Gly
        690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
                725                 730                 735

Ser Gly Val Thr Ile Ala Met Ser Asp Val Leu Val Leu Pro Asn Lys
            740                 745                 750

Glu Glu Met Leu Asp Arg Tyr Glu Glu Ser Ala Arg Gln Ile Glu Val
        755                 760                 765

Lys Tyr Asn Arg Gly Lys Leu Thr Gly Arg Glu Arg Tyr Asp Arg Leu
770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
                805                 810                 815

Ala Ala Gly Asn Met Arg Gln Ile Trp Thr Leu Ala Gly Met Lys Gly
```

```
                820                 825                 830
Met Val Val Asn Ser Lys Gly Asp Tyr Ile Thr Arg Pro Ile Lys Thr
            835                 840                 845
Ser Phe Arg Glu Gly Leu Thr Val Leu Glu Tyr Phe Asn Asn Ser His
        850                 855                 860
Gly Ser Arg Lys Gly Leu Ala Asp Thr Ala Leu Arg Thr Ala Asp Ser
865                 870                 875                 880
Gly Tyr Leu Thr Arg Arg Leu Val Asp Val Ala Gln Asp Val Ile Val
                885                 890                 895
Arg Val Glu Asp Cys Gly Thr Arg Gln Gly Val Arg Val Pro Val Ala
            900                 905                 910
Ala Glu Val Leu Asp Ala Thr Gly Ala Val Thr Gly Tyr Thr Arg His
        915                 920                 925
Asp Leu Ile Glu Thr Ser Val Ser Gly Arg Val Leu Ala Gly Asp Ala
        930                 935                 940
Thr Asn Ala Ala Gly Glu Val Val Leu Ala Ala Gly Thr Asp Leu Thr
945                 950                 955                 960
Glu Leu Asn Ile Asp Leu Leu Val Glu Ala Gly Ile Lys Asp Val Lys
                965                 970                 975
Val Arg Ser Val Leu Thr Cys Gln Thr Pro Thr Gly Val Cys Ala Lys
            980                 985                 990
Cys Tyr Gly Lys Ser Met Ala Ser Gly Gln Gln Val Asp Ile Gly Glu
        995                 1000                1005
Ala Val Gly Ile Val Ala Ala Gln Arg Ile Gly Glu Pro Gly Thr Gln
        1010                1015                1020
Leu Thr Met Arg Thr Phe His Gln Gly Gly Val Gly Gly Asp Ile Thr
1025                1030                1035                1040
Gly Gly Leu Pro Arg Val Gln Glu Leu Phe Glu Ala Arg Val Pro Lys
                1045                1050                1055
Asn Cys Ala Pro Ile Ala Ser Val Glu Gly Val Ile His Leu Glu Asp
            1060                1065                1070
Glu Gly Asn Phe Tyr Thr Leu Thr Ile Val Pro Asp Asp Gly Ser Asp
        1075                1080                1085
Asn Val Val Tyr Glu Lys Leu Ser Lys Arg Gln Gly Leu Ala Ser Thr
    1090                1095                1100
Arg Val Ala Met Glu Ser Asn Ala Gly Ala Phe Ile Glu Arg Thr Leu
1105                1110                1115                1120
Thr Glu Gly Asp Arg Val Thr Val Gly Gln Arg Leu Leu Arg Gly Ala
                1125                1130                1135
Ala Asp Pro His Asp Val Leu Glu Ile Leu Gly Arg Arg Gly Val Glu
            1140                1145                1150
Gln His Leu Ile Asp Glu Val Gln Ala Val Tyr Arg Ala Gln Gly Val
        1155                1160                1165
Ala Ile His Asp Lys His Ile Glu Ile Ile Arg Gln Met Leu Arg
        1170                1175                1180
Arg Gly Thr Val Ile Glu Ser Gly Ser Thr Glu Phe Leu Pro Gly Ser
1185                1190                1195                1200
Leu Val Asp Leu Ser Glu Ala Lys Leu Ala Asn Ser Glu Ala Ile Gly
                1205                1210                1215
Ala Gly Gly Gln Pro Ala Glu Leu Arg Ser Glu Ile Met Gly Ile Thr
            1220                1225                1230
Lys Ala Ser Thr Ala Thr Glu Ser Trp Leu Ser Ala Ala Ser Phe Gln
        1235                1240                1245
```

Glu Thr Thr Arg Val Leu Thr Asp Ala Ala Ile Asn Lys Arg Ser Asp
            1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
                1285                1290                1295

Glu Ala Ala Arg Asn Ala Ala Tyr Ser Ile Pro Thr Tyr Gly Glu Ser
            1300                1305                1310

Ile Tyr Gly Asp Asp Gly Phe Gly Glu Phe Thr Gly Ala Ser Val Pro
        1315                1320                1325

Leu Asp Glu Ala Phe
    1330

<210> SEQ ID NO 27
<211> LENGTH: 1333
<212> TYPE: PRT
<213> ORGANISM: Artificial Sequence
<220> FEATURE:
<223> OTHER INFORMATION: RpoC of KCCM11016P-rpoC(M20)

<400> SEQUENCE: 27

Met Leu Asp Val Asn Val Phe Asp Glu Leu Arg Ile Gly Leu Ala Thr
  1               5                  10                  15

Ala Asp Asp Ile Arg Arg Trp Ser Lys Gly Glu Val Lys Lys Pro Glu
                20                  25                  30

Thr Ile Asn Tyr Arg Thr Leu Lys Pro Glu Lys Asp Gly Leu Phe Cys
            35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Asp Leu Ile
        115                 120                 125

Ile Tyr Phe Gly Ala Asn Ile Ile Thr Ser Val Asp Glu Glu Ala Arg
    130                 135                 140

His Ser Asp Gln Thr Thr Leu Glu Ala Glu Met Leu Leu Glu Lys Lys
145                 150                 155                 160

Asp Val Glu Ala Asp Ala Glu Ser Asp Ile Ala Glu Arg Ala Glu Lys
                165                 170                 175

Leu Glu Glu Asp Leu Ala Glu Leu Glu Ala Ala Gly Ala Lys Ala Asp
            180                 185                 190

Ala Arg Arg Lys Val Gln Ala Ala Asp Lys Glu Met Gln His Ile
        195                 200                 205

Arg Glu Arg Ala Gln Arg Glu Ile Asp Arg Leu Asp Glu Val Trp Gln
    210                 215                 220

Thr Phe Ile Lys Leu Ala Pro Lys Gln Met Ile Arg Asp Glu Lys Leu
225                 230                 235                 240

Tyr Asp Glu Leu Ile Asp Arg Tyr Glu Asp Tyr Phe Thr Gly Gly Met
                245                 250                 255

Gly Ala Glu Ser Ile Glu Ala Leu Ile Gln Asn Phe Asp Leu Asp Ala
            260                 265                 270

```
Glu Ala Glu Glu Leu Arg Asp Ile Ile Asn Asn Gly Lys Gly Gln Lys
            275                 280                 285

Lys Met Arg Ala Leu Lys Arg Leu Lys Val Val Ala Ala Phe Gln Arg
        290                 295                 300

Ser Gly Asn Asp Pro Ala Gly Met Val Leu Asn Ala Ile Pro Val Ile
305                 310                 315                 320

Pro Pro Glu Leu Arg Pro Met Val Gln Leu Asp Gly Arg Phe Ala
                325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
            355                 360                 365

Asn Glu Lys Arg Met Leu Gln Glu Ser Val Asp Ala Leu Phe Asp Asn
        370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
            405                 410                 415

Leu Leu Gly Lys Arg Val Asp Tyr Ser Gly Arg Ser Val Ile Ile Val
            420                 425                 430

Gly Pro Gln Leu Arg Leu His Glu Cys Gly Leu Pro Lys Leu Met Ala
            435                 440                 445

Leu Glu Leu Phe Lys Pro Phe Val Met Lys Arg Leu Val Glu Asn Glu
        450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
                485                 490                 495

Met Leu Asn Arg Ala Pro Thr Leu His Arg Leu Gly Ile Gln Ala Phe
            500                 505                 510

Glu Pro Val Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Val Leu Met Leu
545                 550                 555                 560

Ala Ser Asn Asn Ile Leu Ser Pro Ala Ser Gly Lys Pro Leu Ala Met
            565                 570                 575

Pro Arg Leu Asp Met Val Thr Gly Leu Tyr Tyr Leu Thr Leu Glu Lys
            580                 585                 590

Ser Ser Glu Glu Phe Gly Gly Gln Gly Ala Tyr Gln Pro Ala Asp Glu
        595                 600                 605

Asn Gly Pro Glu Lys Gly Val Tyr Ser Ser Leu Ala Glu Ala Ile Met
610                 615                 620

Ala Tyr Asp Arg Gly Val Leu Gly Leu Gln Ala Pro Val Arg Ile Arg
625                 630                 635                 640

Leu Asn His Leu Arg Pro Pro Ala Glu Val Glu Ala Glu Gln Phe Pro
            645                 650                 655

Asp Gly Trp Asn Gln Gly Glu Thr Trp Leu Ala His Thr Thr Leu Gly
            660                 665                 670

Arg Val Met Phe Asn Glu Ile Leu Pro Trp Asn Tyr Pro Tyr Leu Glu
            675                 680                 685
```

```
Gly Val Met Val Arg Lys Gly Gly Ser Asp Lys Ile Met Leu Gly
    690                 695                 700

Asp Val Val Asn Asp Leu Ala Ala Lys Tyr Pro Met Ile Thr Val Ala
705                 710                 715                 720

Gln Thr Met Asp Lys Met Lys Asp Ala Gly Phe Tyr Trp Ser Thr Arg
            725                 730                 735

Ser Gly Val Thr Ile Ala Met Ser Asp Val Leu Val Leu Pro Asn Lys
        740                 745                 750

Glu Glu Met Leu Asp Arg Tyr Glu Glu Ser Ala Arg Gln Ile Glu Val
            755                 760                 765

Lys Tyr Asn Arg Gly Lys Leu Thr Gly Arg Glu Arg Tyr Asp Arg Leu
    770                 775                 780

Val Glu Leu Trp Lys Asp Ala Thr Asp Glu Val Gly Gln Ala Val Glu
785                 790                 795                 800

Asp Leu Tyr Pro Asp Asp Asn Pro Ile Pro Met Ile Val Lys Ser Gly
            805                 810                 815

Ala Ala Gly Asn Met Arg Gln Ile Trp Thr Leu Ala Gly Met Lys Gly
        820                 825                 830

Met Val Val Asn Ser Lys Gly Asp Tyr Ile Thr Arg Pro Ile Lys Thr
    835                 840                 845

Ser Phe Arg Glu Gly Leu Thr Val Leu Glu Tyr Phe Asn Asn Ser His
    850                 855                 860

Gly Ser Arg Lys Gly Leu Ala Asp Thr Ala Leu Arg Thr Ala Asp Ser
865                 870                 875                 880

Gly Tyr Leu Thr Arg Arg Leu Val Asp Val Ala Gln Asp Val Ile Val
            885                 890                 895

Arg Val Glu Asp Cys Gly Thr Arg Gln Gly Val Arg Val Pro Val Ala
        900                 905                 910

Ala Glu Val Leu Asp Ala Thr Gly Ala Val Thr Gly Tyr Thr Arg His
    915                 920                 925

Asp Leu Ile Glu Thr Ser Val Ser Gly Arg Val Leu Ala Gly Asp Ala
    930                 935                 940

Thr Asn Ala Ala Gly Glu Val Leu Ala Ala Gly Thr Asp Leu Thr
945                 950                 955                 960

Glu Leu Asn Ile Asp Leu Leu Val Glu Ala Gly Ile Lys Asp Val Lys
            965                 970                 975

Val Arg Ser Val Leu Thr Cys Gln Thr Pro Thr Gly Val Cys Ala Lys
            980                 985                 990

Cys Tyr Gly Lys Ser Met Ala Ser Gly Gln Gln Val Asp Ile Gly Glu
    995                 1000                1005

Ala Val Gly Ile Val Ala Ala Gln Ser Ile Gly Glu Pro Gly Thr Gln
    1010                1015                1020

Leu Thr Met Arg Thr Phe His Gln Gly Gly Val Gly Gly Asp Ile Thr
1025                1030                1035                1040

Gly Gly Leu Pro Arg Val Gln Glu Leu Phe Glu Ala Arg Val Pro Lys
            1045                1050                1055

Asn Cys Ala Pro Ile Ala Ser Val Glu Gly Val Ile His Leu Glu Asp
        1060                1065                1070
```

Glu Gly Asn Phe Tyr Thr Leu Thr Ile Val Pro Asp Asp Gly Ser Asp
     1075                1080                1085

Asn Val Val Tyr Glu Lys Leu Ser Lys Arg Gln Gly Leu Ala Ser Thr
    1090                1095                1100

Arg Val Ala Met Glu Ser Asn Ala Gly Ala Phe Ile Glu Arg Thr Leu
1105                1110                1115                1120

Thr Glu Gly Asp Arg Val Thr Val Gly Gln Arg Leu Leu Arg Gly Ala
                1125                1130                1135

Ala Asp Pro His Asp Val Leu Glu Ile Leu Gly Arg Arg Gly Val Glu
            1140                1145                1150

Gln His Leu Ile Asp Glu Val Gln Ala Val Tyr Arg Ala Gln Gly Val
    1155                1160                1165

Ala Ile His Asp Lys His Ile Glu Ile Ile Arg Gln Met Leu Arg
    1170                1175                1180

Arg Gly Thr Val Ile Glu Ser Gly Ser Thr Glu Phe Leu Pro Gly Ser
1185                1190                1195                1200

Leu Val Asp Leu Ser Glu Ala Lys Leu Ala Asn Ser Glu Ala Ile Gly
                1205                1210                1215

Ala Gly Gly Gln Pro Ala Glu Leu Arg Ser Glu Ile Met Tyr Ile Thr
            1220                1225                1230

Lys Ala Ser Leu Ala Thr Glu Ser Trp Leu Ser Ala Ala Ser Phe Gln
    1235                1240                1245

Glu Thr Thr Arg Val Leu Thr Asp Ala Ala Ile His Lys Arg Ser Asp
    1250                1255                1260

Lys Leu Ile Gly Leu Lys Glu Asn Val Ile Ile Gly Lys Leu Ile Pro
1265                1270                1275                1280

Ala Gly Thr Gly Ile Ser Arg Tyr Arg Asn Ile Ser Ile Lys Pro Thr
            1285                1290                1295

Glu Ala Ala Arg Asn Ala Ala Tyr Ser Ile Pro Thr Tyr Gly Glu Ser
        1300                1305                1310

Ile Tyr Gly Asp Asp Gly Phe Gly Glu Phe Thr Gly Ala Ser Val Pro
    1315                1320                1325

Leu Asp Glu Ala Phe
    1330

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
tttgaattct accttgaggg cgttatggt                                    29

<210> SEQ ID NO 29
<211> LENGTH: 29
<212> TYPE: DNA
<213> ORGANISM: Artificial Sequence
<220> FEATURE:
<223> OTHER INFORMATION: primer

<400> SEQUENCE: 29
tttgaattcc cgttggtcag cgtctgctc                                    29

<210> SEQ ID NO 30
<211> LENGTH: 29
<212> TYPE: DNA

```
<213> ORGANISM: Artificial Sequence
<220> FEATURE:
<223> OTHER INFORMATION: primer

<400> SEQUENCE: 30
tttgtcgacc agggcctcaa cttctcagc                                    29
```